US008309583B2

(12) United States Patent
Codd et al.

(10) Patent No.: US 8,309,583 B2
(45) Date of Patent: Nov. 13, 2012

(54) DESFERRIOXAMINE CONJUGATES, DERIVATIVES AND ANALOGUES

(76) Inventors: Rachel Codd, Croydon (AU); Liam Grant Schipanski, Warners Bay (AU)

( * ) Notice: Subject to any disclaimer, the term of this patent is extended or adjusted under 35 U.S.C. 154(b) by 224 days.

(21) Appl. No.: 12/740,957

(22) PCT Filed: Oct. 31, 2008

(86) PCT No.: PCT/AU2008/001617
§ 371 (c)(1),
(2), (4) Date: Apr. 30, 2010

(87) PCT Pub. No.: WO2009/055863
PCT Pub. Date: May 7, 2009

(65) Prior Publication Data
US 2010/0273847 A1  Oct. 28, 2010

(30) Foreign Application Priority Data
Nov. 1, 2007  (AU) ................. 2007905998

(51) Int. Cl.
*A61K 31/44* (2006.01)
*A61K 31/41* (2006.01)
*A61K 31/015* (2006.01)
*C07D 213/69* (2006.01)
*C07D 249/08* (2006.01)

(52) U.S. Cl. ........ 514/345; 514/383; 514/766; 546/296; 548/265.8

(58) Field of Classification Search ................ 514/345, 514/383, 766; 546/296; 548/265.8
See application file for complete search history.

(56) References Cited

U.S. PATENT DOCUMENTS
5,624,901 A  4/1997 Raymond et al.
5,807,879 A  9/1998 Rosebrough et al.

FOREIGN PATENT DOCUMENTS
WO  WO 93/15093  8/1993
WO  WO 00/36422  6/2000
WO  WO 2005/023310 A2  3/2005
WO  WO 2006/014530  2/2006
WO  WO 2007/038346  4/2007
WO  WO 2008/015021  2/2008

OTHER PUBLICATIONS

Fleming RE, Ponka P. Iron overload in human disease. N. Engl J Med. Jan. 26, 2012;366(4):348-59.*
Rivera-Mancía S, Pérez-Neri I, Ríos C, Tristán-López L, Rivera-Espinosa L, Montes S. The transition metals copper and iron in neurodegenerative diseases. Chem Biol Interact. Jul. 30, 2010;186(2):184-99.*
Siddique A, Kowdley KV. Review article: the iron overload syndromes. Aliment Pharmacol Ther. Apr. 2012;35(8):876-93.*
International Search Report in corresponding PCT/AU2008/001617 dated Jan. 7, 2009.
Written Opinion in Corresponding PCT/AU2008/001617 dated Dec. 16, 2008.
International Preliminary Report on Patentability in Corresponding PCT/AU2008/001617 dated May 4, 2010.
Hou et al., "Potentiometric, Spectrophotometric, and $^1$H NMR Study of Four Desferrioxamine B Derivatives and Their Ferric Complexes," *J. Am. Chem. Soc. 116*, 840-846, 1994.
Palanche et al., "Fluorescent siderophore-based chemosensors: iron (III) quantitative determinations," *JBIC 4*, 188-198, 1999.
Rodgers, et al., Ferric Ion Sequestering Agents. 11. Synthesis and Kinetics of Iron Removal from Transferrin of Catechoyl Derivatives of Desferrioxamine B$^1$, *J. Med. Chem 26*, 439-442, 1983.
Guilmette et al., "Competitive Binding of Pu and Am with Bone Mineral and Novel Chelating Agents," *Radiation Protection Disimetry 105*(1-4), 527-534, 2003.
Ihnat et al., "Synthesis and Solution Properties of Deferoxamine Amides," *J. Pharm. Soc. 89*(12), 1525-1536, Dec. 2000.
Diarra et al., "Species Selectivity of New Siderophore-Drug Conjugates that Use Specific Iron Uptake for Entry into Bacteria," *Antimicrobial Agents and Chemotherapy 40*(11), 2610-2617, Nov. 1996.
Moggia et al., "Design, synthesis and redox properties of two ferrocene-containing iron chelators," *Tetrahedron Letters 47*, 3371-3374, 2006.
Arano et al., "A Novel Bifunctional Metabolizable Linker for the Conjugation of Antibodies with Radionuclides," *Bioconjugate Chem.*, 2:71-76 (1991).
Ardon et al., "Iron Uptake in Ustilago Maydis: Tracking the Iron Path," Journal of Bacteriology, 180(8):2021-2026 (1998).
Bickel et al., "Stoffwechselprodukte von Mikroorganismen—53 ueber die Konstitution von Ferrimycin A1," Tetrahedron, Suppl. 8(1):171-179 (1966).
Bickel et al., "Stoffwechselprodukte von Mikroorganismen. 43. Mitteilung. Zur Kenntnis von Desferrioxamin B," Helvetica Chimica ACTA, 46(4):1385-1389 (1963).
Buss et al., "Lipophilicity of analogs of pyridoxal isonicotinoyl hydrazone (PIH) determines the efflux of iron complexes and toxicity in K562 cells," Biochemical Pharmacology, 65:349-360 (2003).
Chimiak et al., "Semisynthese von Phenolderivaten des Desferri-Ferrioxamins B," Zeitschrift Fuer Chemie, Deutscher Verlag Fuer Grundstoffindustrie GMBH, 25(9):329-330 (1985).
European Search Report for EP 08 84 5967, dated Aug. 23, 2011.

(Continued)

*Primary Examiner* — Paul Zarek
(74) *Attorney, Agent, or Firm* — Marshall, Gerstein & Borun LLP

(57) ABSTRACT

The present invention relates to desferoxamine conjugates, derivatives and analogues thereof. In particular, the present invention relates to desferoxamine conjugates, analogues and derivatives thereof, and methods for reducing levels of metals, especially iron, in a mammal. Uses of the compounds according to the invention are also provided. Compounds of the present invention may also be used to treat iron dyshomeostasis disorders, cancer, malaria and fungal infections. The compounds of the invention may be formulated into a pharmaceutical composition or packaged into kits.

17 Claims, 21 Drawing Sheets

OTHER PUBLICATIONS

Ghosh et al., "Synthesis, Bioactivity, and DNA-Cleaving Ability of Desferrioxamine B-Nalidixic Acid and Anthraquinone Carboxylic Acid Conjugates," Bioorganic & Medicinal Chemistry Letters, 5(20):2337-2340 (1995).

Gorak, R.D., "The Reaction of Deferoxamine with Organic Acid Chlorides," Soviet Progress in Chemistry, 55(11):107-109 (1989).

Hershko, C., "Iron Chelators for Thalassaemia," Birtish Journal of Haematology, 101 (3):399-406 (1998).

Hsieh et al., "Direct Solid-Phase Synthesis of Octreotide Conjugates: Precursors for Use as Tumor-Targeted Radiopharmaceuticals," Bioorganic & Medicinal Chemistry, 7:1797-1803 (1999).

Keller-Schierlein et al., "Stoffwechselprodukte von Mikroorganismen. 49. Mitteilung. Die Ferrioxamine A1, A2 and D2," Helvetica Chimica Acta, 48(4):710-723 (1965).

Koizumi et al., "67Ga-labeled Antibodies for Immunoscintigraphy and Evaluation of Tumor Targeting of Drug-Antibody Conjugates in Mice," Cancer Research, 48(5):1189-1194 (1988).

Laub et al., "Cellular Pharmacology of Deferrioxamine B and Derivatives in Cultured Rat Hepatocytes in Relation to Iron Mobilization," Biochemical Pharmacology, 34(8):1175-1183 (1985).

Lytton et al., "Reversed Siderophores as Antimalarial Agents. II. Selective Scavenging of Fe(III) from Parasitized Erythrocytes by a Fluorescent Derivative of Desferal," Molecular Pharmacology, 40(4):584-590 (1991).

Muetterties et al., "Ferrioxamine B Derivatives as Hepatobiliary Contrast Agents for Magnetic Resonance Imaging," Magnetic Resonance in Medicine, 22:88-100 (1991).

Ng et al., "Ferric Ion Sequestering Agents. 21.1 Synthesis and Spectrophotometric and Potentiometric Evaluation of Trihydroxamate Analogues of Ferrichrome," Inorg. Chem., 28:2062-2066 (1989).

Olivieri et al., "Iron-Chelation Therapy with Oral Derferiprone in Patients with Thalassemia Major," The New England Jour. of Med., 332(14):918-922 (1995).

Pochon et al., "A Novel Derivative of the Chelon Desferrioxamine for Site-Specific Conjugation to Antibodies," Int. J. Cancer, 43:1188-1194 (1989).

Prelog et al., "Stoffwechselprodukte von Actinomyceten. 36. Mitteilung. Uber die Synthese der Ferrioxamine B und $D_1$," Helvetica Chimica Acta, 75:631-637 (1962).

Rosebrough, S., "Plasma Stability and Pharmacokinetics of Radiolabeled Deferoxamine-Biotin Derivatives," Jour. of Phar. and Exper. Thera., 265(1):408-415 (1993).

Sato et al., "Synthesis and Characterization of Superoxide Dismutase—Deferoxamine Conjugate via Polyoxyethylene: A New Molecular Device for Removal of a Variety of Reactive Oxygen Species," Bioconjugate Chemistry, 6:249-254 (1995).

Srinivas et al., "Stoffwechselprodukte von Microorganismen. 216. Mitteilung. Isolierung, Strukturaufklarung und Synthese von Ferrioxamin H," Helvetica Chimica Acta, 6:1818-1824 (1982).

Wang et al., "Synthesis, Purification, and Tumor Cell Uptake of $^{67}$Ga-Deferoxamine-Folate, a Potential Radiopharmaceutical for Tumor Imaging," Bioconjugate Chem., 7:56-62 (1996).

Xu et al., "Specific Sequestering Agents for the Actinides. 28. Synthesis and Initial Evaluation of Multidentate 4-Carbamoyl-3-hydroxy-1-methyl-2(1$H$)-pyridinone Ligands for in Vivo Plutonium (IV) Chelation," J. Med. Chem., 38:2606-2614 (1995).

Yu et al., "Chelators at the Cancer Coalface: Desferrixamine to Triapine and Beyond," Clin. Cancer Res., 12:6876-6883 (2006).

Zanninelli et al., "Chelation and Mobilization of Cellular Iron by Different Classes of Chelators," Molecular Pharmacology, 51:842-852 (1997).

* cited by examiner

Iron bound by DFOB 1:1 ratio

ICL670

II

Tridentate (deferasirox)

L1

III

Bidentate (deferiprone)

Desferadax

DESFERRIOXAMINE CONJUGATES, DERIVATIVES AND ANALOGUES

CROSS-REFERENCE TO RELATED APPLICATIONS

This application is a U.S. National Phase application based on PCT/AU2008/001617, filed Oct. 31, 2008, which claims priority to Australian Patent Application No. 2007905998 filed Nov. 1, 2007.

FIELD OF THE INVENTION

The present invention relates to desferrioxamine conjugates, derivatives and analogues thereof. In particular, the present invention relates to desferrioxamine conjugates, analogues and derivatives thereof, and methods for reducing levels of metals, especially iron, in a mammal. However, it will be appreciated that the invention is not limited to this particular field of use.

BACKGROUND OF THE INVENTION

The following discussion of the prior art is provided to place the invention in an appropriate technical context and enable the advantages of it to be more fully understood. However, it should be appreciated that any discussion of the prior art throughout the specification should not be considered as an express or implied admission that such prior art is widely known or forms part of common general knowledge in the field.

Iron is crucial for maintaining normal structure and function of virtually all mammalian cells (see, for example, Voest et al., in *Ann. Intern. Med.*, 120:490-499 (1994) and Kontoghiorghes, G. J., in *Toxicol. Letters*, 80:1-18 (1995)). Iron and its binding proteins have immunoregulatory properties, and adult humans contain 3-5 g of iron, mainly in the form of haemoglobin (58%), ferritin/haemosiderin (30%), myoglobin (9%) and other haem or non-haem enzyme proteins (Harrison and Hoare, in *Metals in Biochemistry*, Chapman and Hall, New York, 1980). Approximately 10 to 15 mg of dietary iron is normally consumed per day by each individual in the U.S. About 1 to 2 mg of iron in the Fe (II) form is absorbed each day chiefly through villi in the duodenum to compensate for the 1 to 2 mg daily body loss of iron. Normal men absorb about 1 mg iron per day, menstruating women 2 mg iron per day, and haemochromatosis patients 2 to 5 mg iron per day.

Total iron levels in the body are regulated mainly through absorption from the intestine and the erythropoietic activity of the bone marrow. Upon absorption, iron is transported to various tissues and organs by the serum protein, transferrin. Once transported to the target tissue or organ, iron is transported and stored intracellularly in the form of ferritin/haemosiderin. Under normal conditions, transferrin is about 30% saturated with iron in healthy individuals, and an equilibrium is maintained between the sites of iron absorption, storage and utilization. The presence of these homeostatic controls ensures the maintenance of physiological levels of not only iron, but also other essential metal ions such as copper, zinc and cobalt. The control of iron absorption may be genetic with complex interactions with intestinal mucosal cells, dietary factors, and other influences.

Iron is absorbed both as haem and non-haem iron chiefly in the duodenum and the proximal jejunum. Iron in meat, primarily haem iron, is better absorbed than non-haem iron. The absorption of haem iron is not influenced by dietary composition or luminal factors as is the absorption of non-haem iron.

Breakdown of these controls could result in metal imbalance and metal overload, causing iron overloading toxicity and possibly death in many groups of patients, especially those with idiopathic haemochromatosis (see, for example, Guyader et al., in *Gastroenterol.*, 97:737-743 (1989)). Shifting of immunoregulatory balances by iron excess or deficiency may produce severe, deleterious psychological effects.

Iron, particularly in the form of free iron ions, can promote the generation of reactive oxygen species through the iron-catalyzed Fenton and Haber-Weiss reactions (Haber and Weiss, in *Proc. R. Soc. Ser. A* 1934; 147:332) as follows:

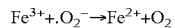

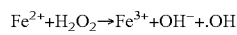

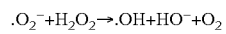

The Haber-Weiss and Fenton reactions are seen to produce the hydroxyl radical (.OH), a highly potent oxidant which is capable of causing oxidative damage to lipids, proteins, and nucleic acids (Lai and Piette. *Biochem Biophys Res-Commun* 1977; 78:51-9, and Dizdaroglu and Bergtold. *Anal Biochem* 1986; 156:182). See also FIG. 3 herein.

The effects of iron overload include decreased antibody-mediated and mitogen-stimulated phagocytosis by monocytes and macrophages, alterations in T-lymphocyte subsets, and modification of lymphocyte distribution in different compartments of the immune system. Accordingly, among its toxic effects, iron is known to mediate a series of oxygen related free radical reactions (see, for example, Halliwell and Gutteridge, in Halliwell and Gutteridge, *Free Radicals in Biology and Medicine*, 2nd edition. Oxford: Clarendon Press, 15-19 (1989)).

In particular, haemochromatosis is a disease of excessive iron storage leading to tissue damage and fibrosis. Both genetic, or hereditary, haemochromatosis, which can affect 1 in 500 of some populations, and the form of this disease which occurs as a secondary consequence of the haemoglobinopathy, homozygous β-thalassemia, with 40 million carriers worldwide, have a common pathology. Haemochromatosis of the liver in man is caused when the iron burden exceeds a threshold in the region of 22 μmol/g liver dry weight.

Genetic haemochromatosis, a life-long disease, is probably the most common autosomal recessive disorder found in white Americans, of who about 5/1,000 (0.5 percent) are homozygous for the associated gene. The haemochromatosis gene is probably located close to the HLA-A locus on the short arm of chromosome 6. Homozygous individuals may develop severe and potentially lethal haemochromatosis, especially after age 39.

Hereditary haemochromatosis involves an increased rate of iron absorption from the gut with subsequent progressive storage of iron in soft organs of the body. Excessive iron storage eventually produces pituitary, pancreatic, cardiac, spleen, epidermal, and liver and/or hepatic failure or cancer. Damage to these organs may be characterized by elevated liver enzyme values and hepatomegaly often with cirrhosis which may develop into hepatocellular carcinoma, splenomegaly, pancreatic fibrosis leading to diabetes mellitus, hyperpigmentation of the skin, pituitary insufficiency, hypogonadism, occasional hypothyroidism, cardiac abnormalities such as arrythmias and/or congestive heart failure, and arthritis/arthropathy. Early diagnosis can prevent these excess iron-induced problems. Iron overload owing to HLA-linked hereditary haemochromatosis can be distinguished from other causes of haemochromatosis by liver biopsies and interpretations.

Iron overload as seen in hereditary haemochromatosis patients enhances suppressor T-cell (CD8) numbers and activity, decreases the proliferative capacity, numbers, and activity of helper T cells (CD4) with changes in CD8/CD4 ratios, impairs the generation of cytotoxic T cells, and alters immunoglobulin secretion when compared to treated hereditary haemochromatosis patients or controls. A correlation has recently been found between low CD8+ lymphocyte numbers, liver damage associated with HCV positivity, and severity of iron overload in β-thalassemia major patients. Iron overload, with its associated increases of serum iron levels and transferrin saturation, may cause a poor response to interferon therapy. Iron overload with hyperferremia is associated with suppressed functions of the complement system (classic or alternative types).

The mesylate salt of desferrioxamine B (Desferal, CAS: 138-14-7; Novartis) is the first-line treatment for patients who suffer from transfusional-dependent iron-overload disease, which occurs as a secondary complication of β-thalassemia. Estimates suggest that 270 million people worldwide are carriers of β-thalassemia and that 200,000 babies are born with the disease each year.

In order to treat β-thalassemia, patients must undergo two or three blood transfusions per month. Since each unit of blood contains approximately 220 mg of iron, this transfusion regime results in an average daily iron intake of 15-22 mg/day, which is significantly in excess of the normal daily intake of 1 mg/day. Iron is able to readily gain access to highly vascularised organs, such as the heart, liver and the endocrine glands; without treatment, transfusional-dependent iron-overload that results from the increased haem catabolism can lead to death, most often from cardiomyopathy.

In order to ameliorate the excess Fe burden, patients with β-thalassemia undergo chelation therapy with Desferal. Desferal has a poor plasma half-life (t½~15 min) due to a combination of poor distribution and rapid clearance—the drug is limited to distribution in the plasma and, therefore, no Desferal reservoir is able to be maintained in other cellular compartments. Desferal is not effective when administered orally (15% of an orally administered dose is absorbed [1]) and patients must undergo subcutaneous infusions with Desferal for up to 70 h per week. The intolerable treatment regime for iron-overload disease leads to poor patient compliance and can lead to premature death. Furthermore, if iron-chelation therapy is discontinued, patients usually die, usually from cardiotoxic events. For example, see FIG. 4 for typical survival curves for patients with thalassemia syndromes comparing various treatment regimens.

The motivation to find orally-available iron chelation agents has lead to the discoveries of deferiprone (L1) and deferasirox (ICL670, 4-[3,5-bis-(2-hydroxyphenyl)-[1,2,4]-triazol-1-yl]benzoic acid); these abiological chelates are used orally in some patients who are not able to take Desferal. While these compounds are orally available, both ICL670 and L1 are less effective than Desferal at binding Fe(III) and have poorer toxicity profiles. Several fatalities in the US from irreversible renal failure following treatment with ICL670 has made the future of this candidate uncertain. Clearly, there is a need for new compounds that are effective at treating iron-overload disease and that have tolerable administration regimes. The poor pharmacological profile of Desferal is largely attributed to the low membrane partition coefficient of the drug—Desferal is very water soluble and is inefficient at crossing the lipid membrane bilayer of cells. This affects the potential for DFOB to access intracellular iron pools which is one of major shortcomings in DFOB-based iron overload treatment.

Furthermore, the Desferal™ treatment regime is not well tolerated by patients since the drug is not substantially orally active and has a relatively short plasma half-life (approx. 15 min) and, therefore, must be administered subcutaneously or intravenously. Indeed, patients can spend up to 70 h per week connected up to a pump for administering chelation therapy (e.g. 14 hrs/day for 5 days/week). Apart from the inconvenience, this also leads to poor compliance in at least 50% of patients. It has been estimated that 200,000 babies are born with thalassaemia major each year. Prior to the development of Desferal™, these patients typically had life expectancies of less than 30 years (70% of all deaths in these patients is due to myocardial disease) and were dependent on life-long blood transfusions.

There still remains a need for an improved treatment of iron overload disease in humans. There is also a need for improved compounds and formulations for the treatment of iron overload disease in humans, and in particular, a need for orally available iron chelators and/or to find drug molecules with less arduous treatment regimes than Desferal™, since a more tolerable treatment regime leads to higher patient compliance and less mortality in patients. Preferably, such drug molecules may have superior pharmacokinetic properties to Desferal™.

SUMMARY OF THE INVENTION

Accordingly, in a first aspect, the present invention provides a compound of formula (I)

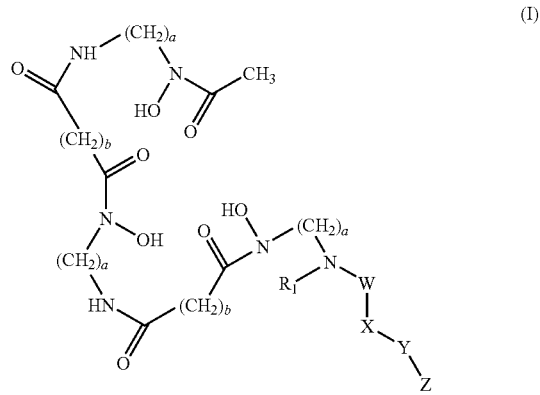

wherein, a is an integer from 2 to 7 wherein any of the $CH_2$ groups in this unit may be substituted with alkyl or aryl units that may contain heteroatoms (S, N, O, Cl, F, Br or I);

b is an integer from 1 to 7 wherein any of the $CH_2$ groups in this unit may be substituted with alkyl or aryl units that may contain heteroatoms (S, N, O, Cl, F, Br or I);

$R_1$ is H or $(CH_2)_n$, where n is an integer from 1 to 6 or is a $CH_2$ linker unit that may be further substituted at any $CH_2$ group in the chain with alkyl or aryl units that may contain heteroatoms (S, N, O, Cl, F, Br or I);

W is C(O) or C(S) or $(CH_2)_n$, where n is 0 or an integer from 1 to 6, wherein when W is C(S) it may be or may not be part of a thiosemicarbazone derivative which includes the two NH groups to which W is bonded, and wherein when W is C(O) it may be or may not be part of a semicarbazone derivative which includes the two NH groups to which W is bonded;

X is NH or (CH$_2$)$_n$, wherein n is 0 or an integer from 1 to 6 or is a CH$_2$ linker unit that may be further substituted at any CH$_2$ group in X with alkyl or aryl units that may contain heteroatoms (S, N, O, Cl, F, Br or I);

Y is absent or is N, O, S, C(O), C(S), S(O), S(O)$_2$, NH or NR' where R' is an alkyl or aryl substituent that may contain heteroatoms (S, N, O, Cl, F, Br or I);

Z is an optionally substituted carbocyclic group or an optionally substituted aliphatic group or an optionally substituted aromatic group or a heterocyclic group or is a derivative of L1 (Ferriprox, 3-hydroxy-1,2-dimethyl-4(1H)-pyridone) or is a derivative of ICL670 (Deferasirox, 4-[3,5-bis(2-hydroxyphenyl)-1H-1,2,4-triazol-1-yl]-benzoic acid) or is a thiosemicarbazone derivative (where W=C(S)) such as 2-(di-2-pyridinylmethylene)-hydrazinecarbothioamide or is a semicarbazone derivative (where W=C(O)); provided that W-X-Y-Z when taken together with the N to which it is attached is not an amide derivative of biotin.

Preferably, when R$_1$ is H and W is CH$_2$ or alternatively, when the compound according to the invention has secondary amine groups, the compound of Formula I may be in the form of a salt, for example a HCl salt.

Preferably, Z is a carbocycle selected from norbornane, cubane, trishomocubane, adamantane, phenyl, biphenyl, naphthyl, tetrahydronaphthyl, indenyl, azulenyl, phenantryl, pyrenyl, each of said carbocycle optionally being substituted with at least one substituent, each substituent independently selected from halo, hydroxyl, =O, C$_{1-6}$alkyl, C$_{1-6}$alkyloxy, C$_{1-6}$alkyloxycarbonyl, C$_{1-6}$alkylcarbonyloxy, C$_{1-6}$alkylthio, polyhalo-C$_{1-6}$alkyl, polyhaloC$_{1-6}$alkyloxy, cyano, nitro, carboxyl, C$_{1-4}$alkyl-SO$_2$-, amino, mono- or di(C$_{1-4}$alkyl)amino, C$_{1-4}$alkylcarbonylamino, or —O(CH$_2$CH$_2$O)$_3$CH$_2$CH$_2$O—; or a heterocycle selected from pyrrolinyl, imidazolinyl, pyrazolinyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, piperidinyl, piperazinyl, morpholinyl, thiomorpholinyl; or a heterocycle selected from indolyl, indolizinyl, isoindolyl, indolinyl, benzofuranyl, benzothienyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthyridinyl, pteridinyl, benzoxadiazolyl, benzoxazolyl, benzthiazolyl, each said heterocycle optionally being substituted with at least one substituent, each substituent independently selected from halo, hydroxyl, =O, C$_{1-6}$alkyl, C$_{1-6}$alkyloxy, C$_{1-6}$alkyloxycarbonyl, C$_{1-6}$alkylcarbonyloxy, C$_{1-6}$alkylthio, polyhalo-C$_{1-6}$alkyl, polyhaloC$_{1-6}$alkyloxy, cyano, nitro, carboxyl, C$_{1-4}$alkyl-SO$_2$-, amino, mono- or di(C$_{1-4}$alkyl)amino, C$_{1-4}$alkylcarbonylamino, or —O(CH$_2$CH$_2$O)$_3$CH$_2$CH$_2$O—.

More preferably, Z is selected from norbornane, adamantane, phenyl or pyridyl optionally being substituted with at least one substituent, each substituent independently selected from halo, hydroxyl, =O, C$_{1-6}$alkyl, C$_{1-6}$alkyloxy, C$_{1-6}$alkyloxycarbonyl, C$_{1-6}$alkylcarbonyloxy, C$_{1-6}$alkylthio, polyhalo-C$_{1-6}$ alkyl, polyhaloC$_{1-6}$alkyloxy, cyano, nitro, carboxyl, C$_{1-4}$alkyl-SO$_2$-, amino, mono- or di(C$_{1-4}$alkyl)amino, C$_{1-4}$alkylcarbonylamino, or —O(CH$_2$CH$_2$O)$_3$CH$_2$CH$_2$O—.

Still more preferably, Z is selected from norbornane, adamantane, phenyl or pyridyl optionally being substituted with at least one substituent, each substituent independently selected from hydroxyl, C$_{1-6}$alkyl, —O(CH$_2$CH$_2$O)$_3$CH$_2$CH$_2$O— or =O.

Preferably, the compound according to the first aspect is selected from:

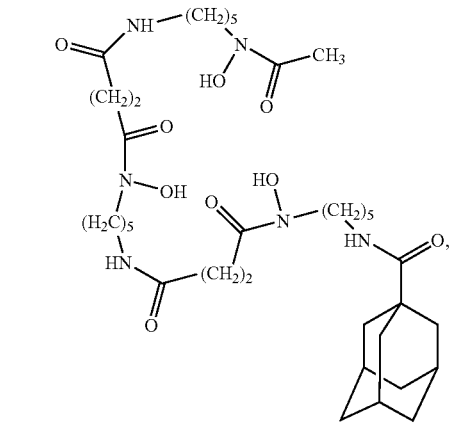

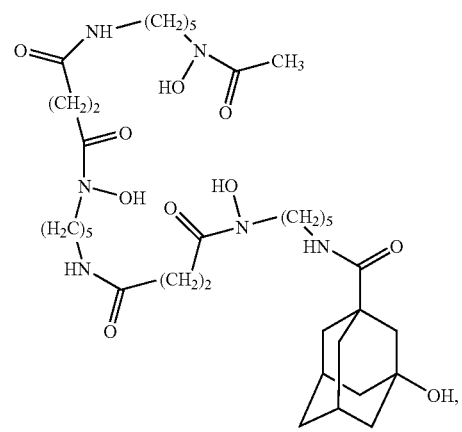

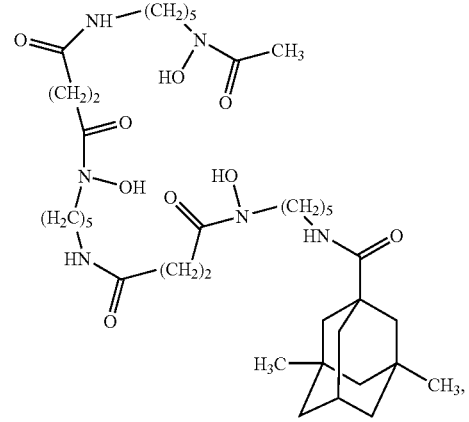

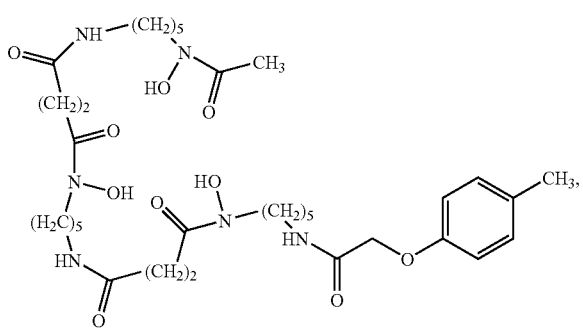

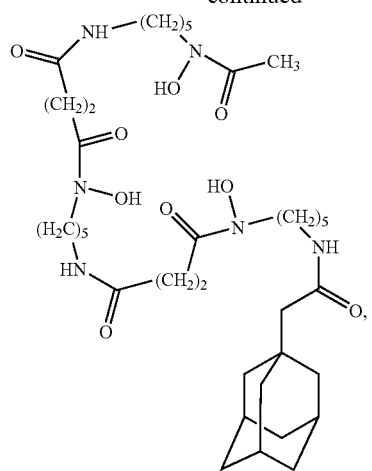
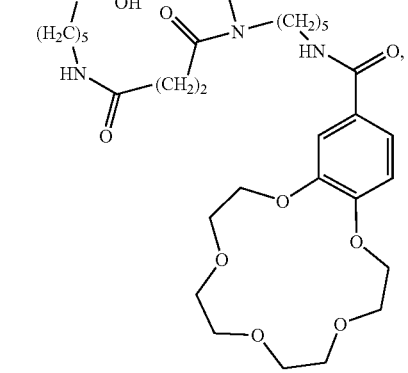
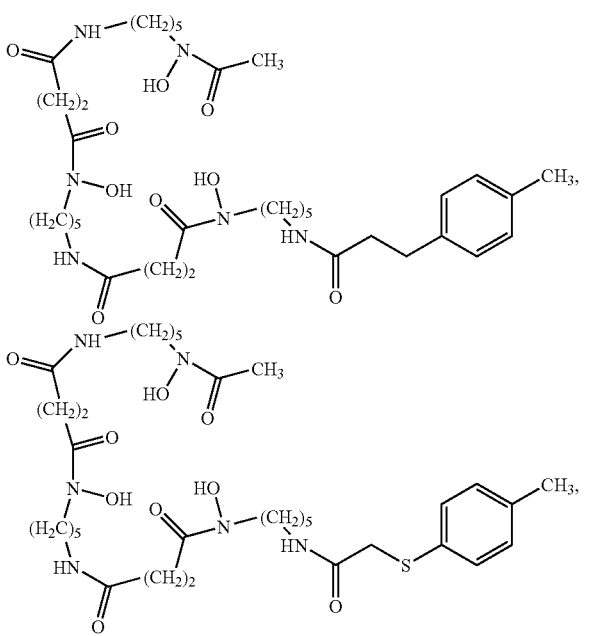
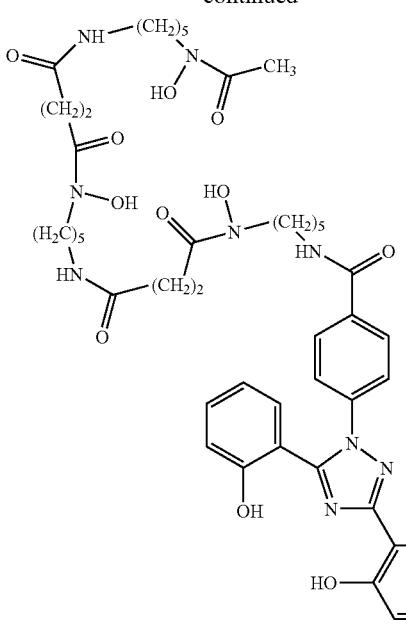
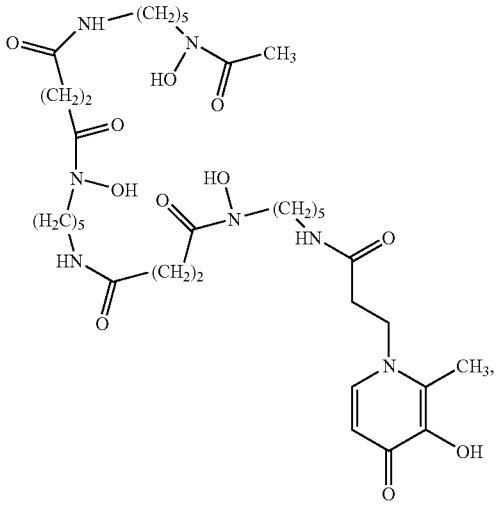
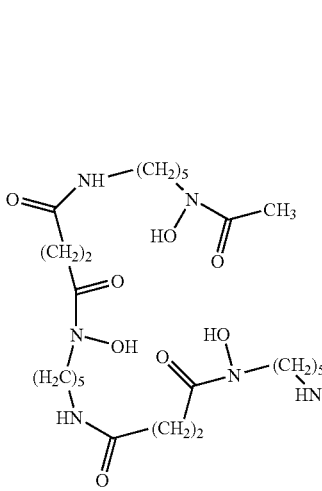
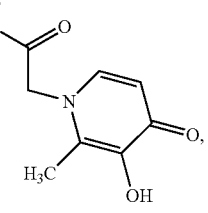

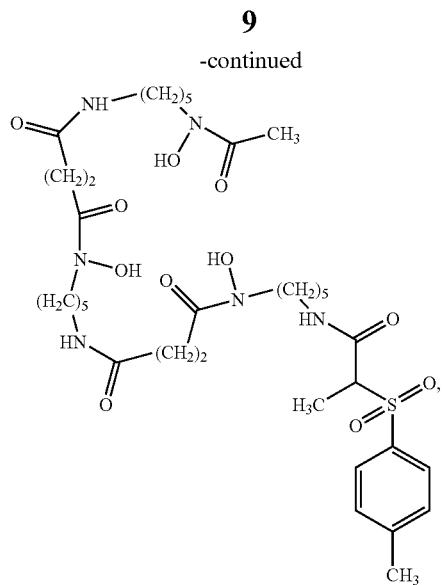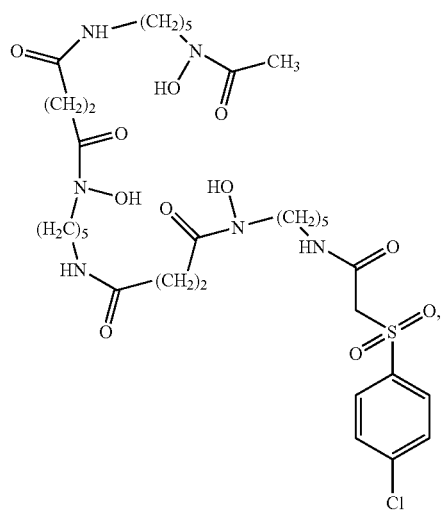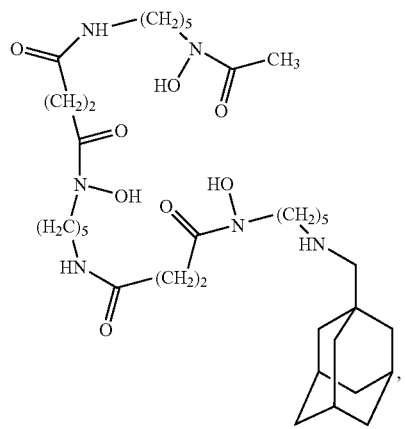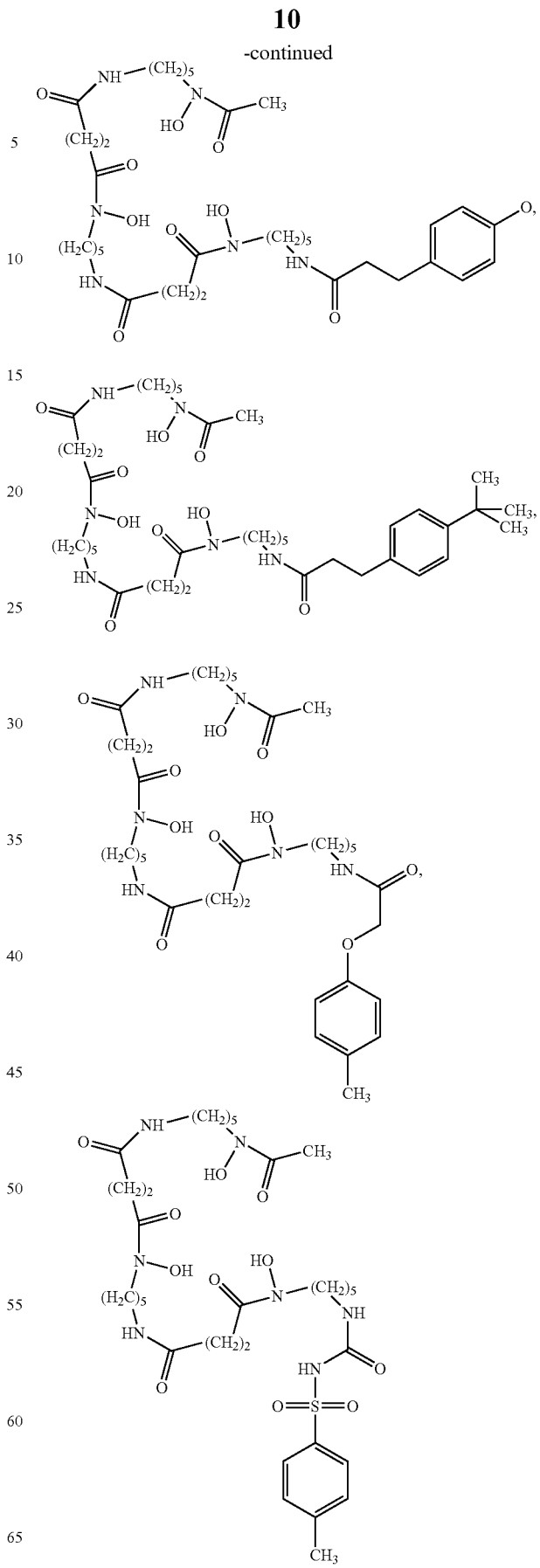

11
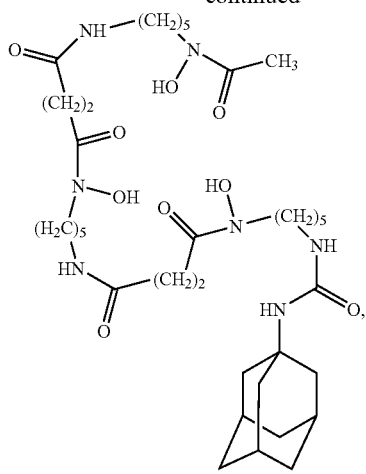
12
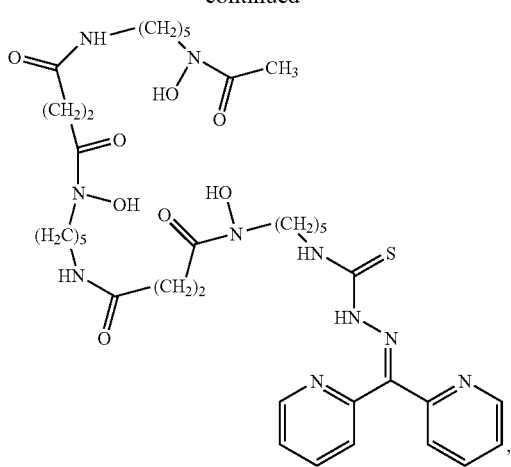
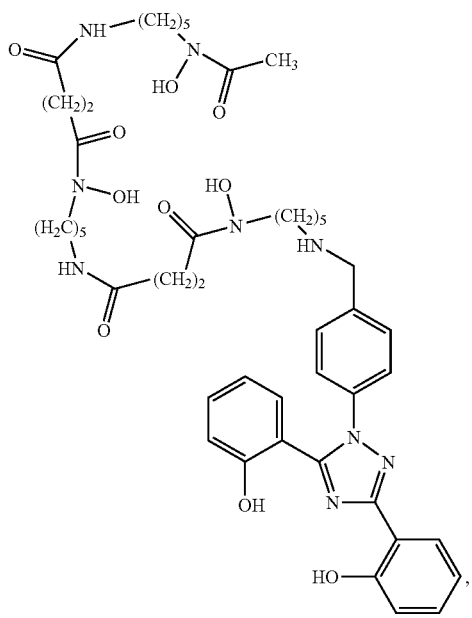
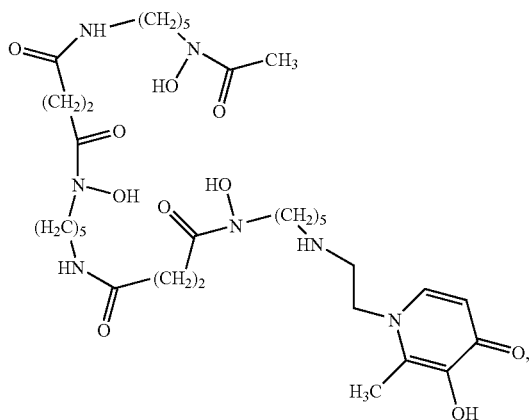
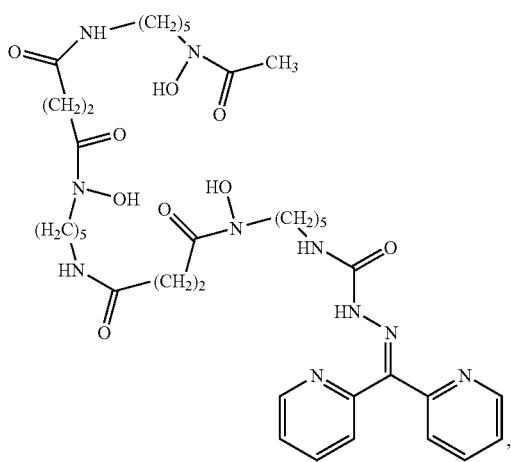

13
-continued
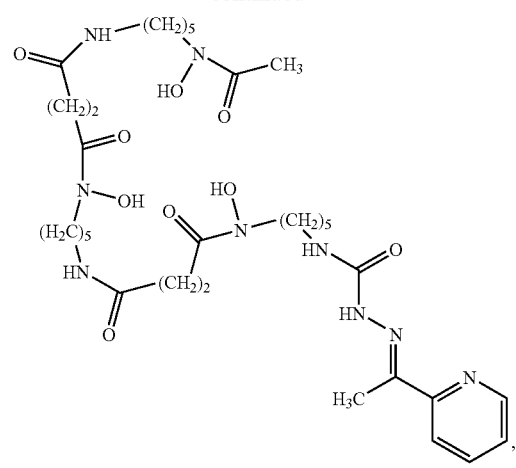
,
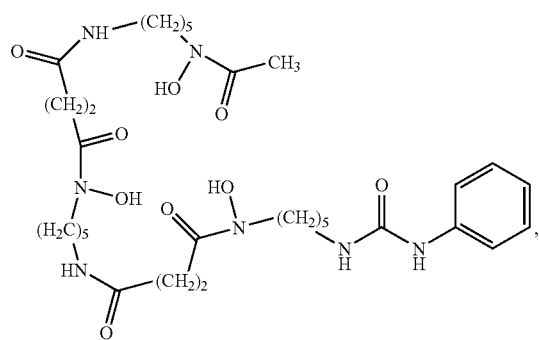
,
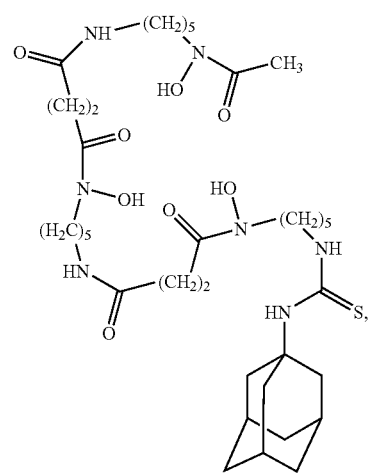
,
14
-continued
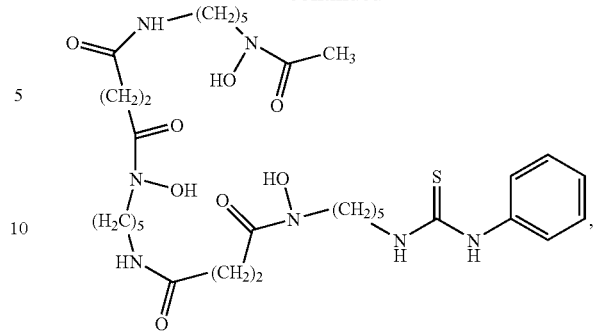
,
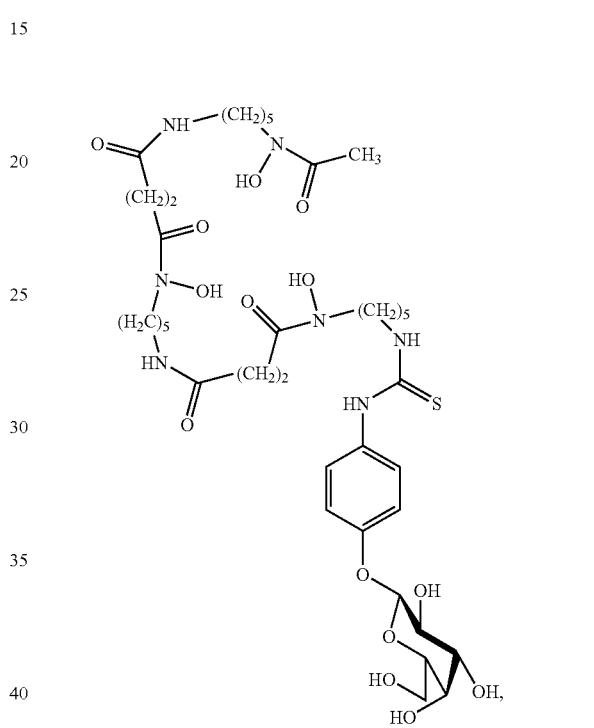
,
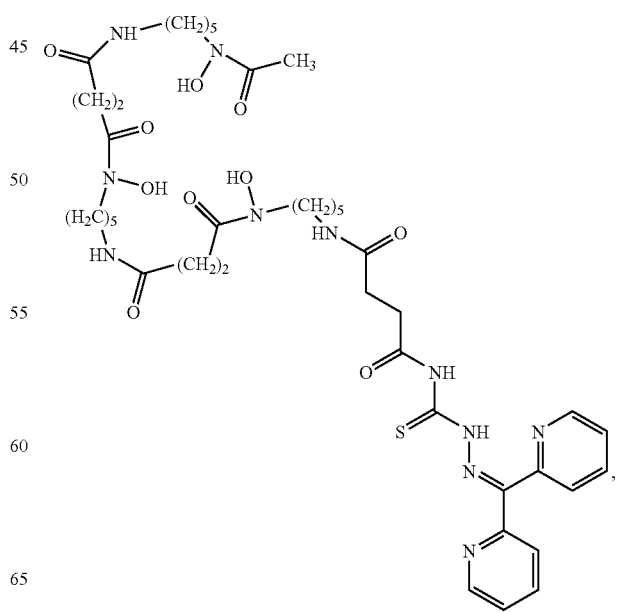
, -continued

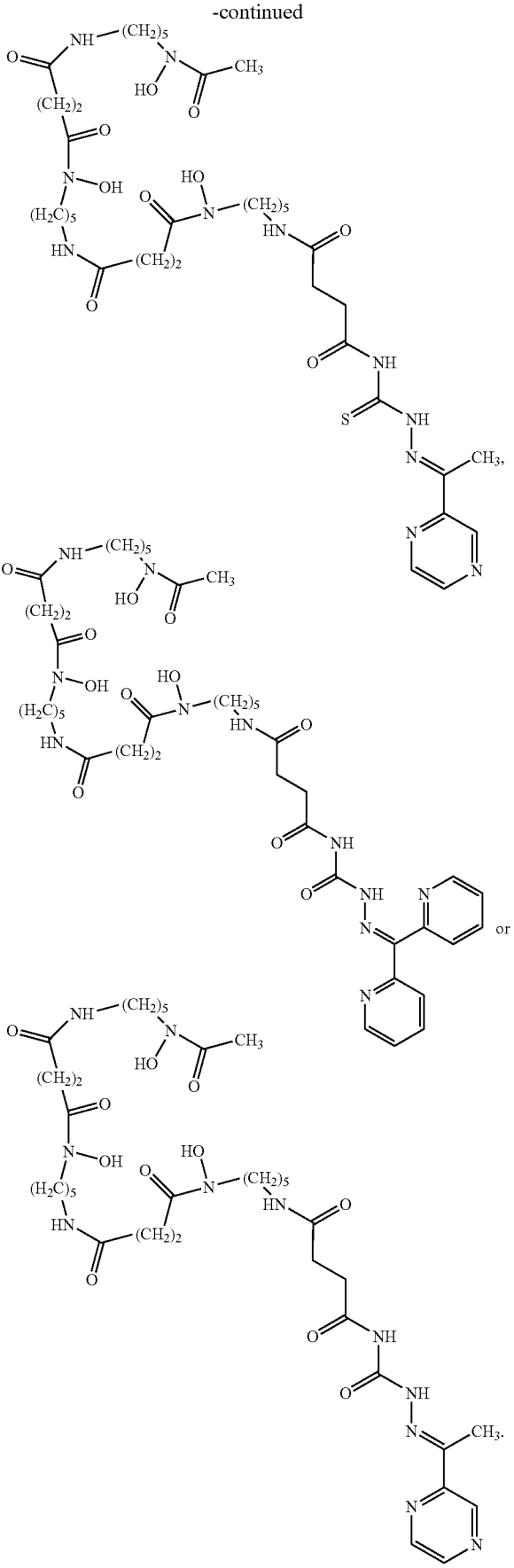

Advantageously, the present Applicant has determined that the compounds of the present invention display similar or improved iron binding efficiency relative to desferrioxamine. Furthermore, the conjugates, analogues and derivatives in accordance with the present invention may be prepared from commercially available chemicals, and the molecular weights of the compounds of the invention are also similar to desferrioxamine.

Advantageously, the compounds in accordance with the present invention are particularly suitable for treating an iron dyshomeostasis disorder. Such a disorder may include a primary or secondary iron-overload disorder.

Accordingly, in a second aspect, the present invention provides a method of treating an iron dyshomeostasis disorder comprising administering an effective amount of a compound according to the invention, or an amide biotin conjugate of formula I.

The primary iron-overload disorder may be selected from Parkinson's disease, Alzheimer's disease, Huntington's disease, haemochromatosis, anaemia, β-thalassaemia, myelodysplastic syndrome, aceruloplasminaemia, Friedreich's ataxia and congenital atransferrinaemia.

Preferably, the haemochromatosis is selected from haemochromatosis type 1, haemochromatosis type 2A, haemochromatosis type 2B, haemochromatosis type 3, haemochromatosis type 4, neonatal haemochromatosis.

The anaemia is preferably selected from sickle cell anaemia or Diamond-Blackfan anaemia.

The secondary iron-overload disorder may be selected from dietary iron overload, long term haemodialysis, chronic liver disease, Hepatitis C infection, alcoholic cirrhosis of the liver, non-alcoholic steatohepatitis or porphyria cutanea tarda.

According to a third aspect, the present invention provides a method of treating cancer comprising administering an effective amount of a compound according to the first aspect, or an amide biotin conjugate of formula I, to a patient in need thereof.

According to a fourth aspect, the present invention provides a method of treating malaria comprising administering an effective amount of a compound according to the first aspect, or an amide biotin conjugate of formula I, to a patient in need thereof.

According to a fifth aspect, the present invention provides a method of treating a fungal infection comprising administering an effective amount of a compound according to the first aspect, or an amide biotin conjugate of formula I, to a patient in need thereof.

According to a sixth aspect, the present invention provides use of a compound according to the invention, or an amide biotin conjugate of formula I, in the manufacture or preparation of a medicament for the treatment of an iron dyshomeostasis disorder.

The iron dyshomeostasis disorder may include a primary or secondary iron-overload disorder.

The primary iron-overload disorder may be selected from Parkinson's disease, Alzheimer's disease, Huntington's disease, haemochromatosis, anaemia, β-thalassaemia, myelodysplastic syndrome, aceruloplasminaemia, Friedreich's ataxia and congenital atransferrinaemia.

Preferably, the haemochromatosis is selected from haemochromatosis type 1, haemochromatosis type 2A, haemochromatosis type 2B, haemochromatosis type 3, haemochromatosis type 4, neonatal haemochromatosis.

The anaemia is preferably selected from sickle cell anaemia or Diamond-Blackfan anaemia.

The secondary iron-overload disorder may be selected from dietary iron overload, long term haemodialysis, chronic liver disease, Hepatitis C infection, alcoholic cirrhosis of the liver, non-alcoholic steatohepatitis or porphyria cutanea tarda.

According to a seventh aspect, the present invention provides use of a compound according to the invention, or an amide biotin conjugate of formula I, in the manufacture or preparation of a medicament for the treatment of cancer.

According to an eighth aspect, the present invention provides use of a compound according to the invention, or an amide biotin conjugate of formula I, in the manufacture or preparation of a medicament for the treatment of malaria.

According to a ninth aspect, the present invention provides use of a compound according to the invention, or an amide biotin conjugate of formula I, in the manufacture or preparation of a medicament for the treatment of a fungal infection.

According to a tenth aspect, the present invention provides a pharmaceutical composition comprising a compound of formula (I)

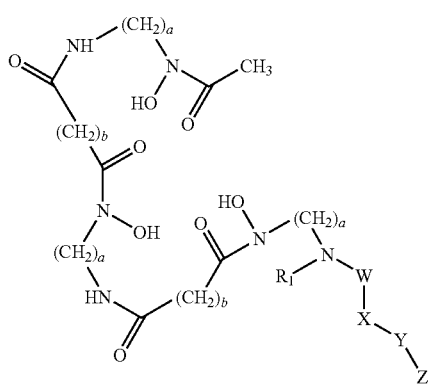

(I)

wherein, a is an integer from 2 to 7 wherein any of the $CH_2$ groups in this unit may be substituted with alkyl or aryl units that may contain heteroatoms (S, N, O, Cl, F, Br or I);

b is an integer from 1 to 7 wherein any of the $CH_2$ groups in this unit may be substituted with alkyl or aryl units that may contain heteroatoms (S, N, O, Cl, F, Br or I);

$R_1$ is H or $(CH_2)_m$, where n is an integer from 1 to 6 or is a $CH_2$ linker unit that may be further substituted at any $CH_2$ group in the chain with alkyl or aryl units that may contain heteroatoms (S, N, O, Cl, F, Br or I);

W is C(O) or C(S) or $(CH_2)_n$, where n is 0 or an integer from 1 to 6, wherein when W is C(S) it may be or may not be part of a thiosemicarbazone derivative which includes the two NH groups to which W is bonded, and wherein when W is C(O) it may be or may not be part of a semicarbazone derivative which includes the two NH groups to which W is bonded;

X is NH or $(CH_2)_n$, wherein n is 0 or an integer from 1 to 6 or is a $CH_2$ linker unit that may be further substituted at any $CH_2$ group in X with alkyl or aryl units that may contain heteroatoms (S, N, O, Cl, F, Br or I);

Y is absent or is N, O, S, C(O), C(S), S(O), $S(O)_2$, NH or NR' where R' is an alkyl or aryl substituent that may contain heteroatoms (S, N, O, Cl, F, Br or I);

Z is an optionally substituted carbocyclic group or an optionally substituted aliphatic group or an optionally substituted aromatic group or a heterocyclic group or is a derivative of L1 (Ferriprox, 3-hydroxy-1,2-dimethyl-4(1H)-pyridone) or is a derivative of ICL670 (Deferasirox, 4-[3,5-bis(2-hydroxyphenyl)-1H-1,2,4-triazol-1-yl]-benzoic acid) or is a thiosemicarbazone derivative (where W=C(S)) such as 2-(di-2-pyridinylmethylene)-hydrazinecarbothioamide or is a semicarbazone derivative (where W=C(O));

or a pharmaceutically acceptable salt thereof, together with a pharmaceutically acceptable excipient, diluent or carrier.

Preferably, Z is a carbocycle selected from norbornane, cubane, trishomocubane, adamantane, phenyl, biphenyl, naphthyl, tetrahydronaphthyl, indenyl, azulenyl, phenantryl, pyrenyl, each of said carbocycle optionally being substituted with at least one substituent, each substituent independently selected from halo, hydroxyl, =O, $C_{1-6}$alkyl, $C_{1-6}$alkyloxy, $C_{1-6}$alkyloxycarbonyl, $C_{1-6}$alkylcarbonyloxy, $C_{1-6}$alkylthio, polyhalo-$C_{1-6}$alkyl, polyhalo$C_{1-6}$alkyloxy, cyano, nitro, carboxyl, $C_{1-4}$alkyl-$SO_2$—, amino, mono- or di($C_{1-4}$alkyl)amino, $C_{1-4}$alkylcarbonylamino, or $O(CH_2CH_2O)_2CH_2CH_2O$; or a heterocycle selected from pyrrolinyl, imidazolinyl, pyrazolinyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, piperidinyl, piperazinyl, morpholinyl, thiomorpholinyl; or a heterocycle selected from indolyl, indolizinyl, isoindolyl, indolinyl, benzofuranyl, benzothienyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthyridinyl, pteridinyl, benzoxadiazolyl, benzoxazolyl, benzthiazolyl, each said heterocycle optionally being substituted with at least one substituent, each substituent independently selected from halo, hydroxyl, =O, $C_{1-6}$alkyl, $C_{1-6}$alkyloxy, $C_{1-6}$alkyloxycarbonyl, $C_{1-6}$alkylcarbonyloxy, $C_{1-6}$alkylthio, polyhalo-$C_{1-6}$alkyl, polyhalo$C_{1-6}$alkyloxy, cyano, nitro, carboxyl, $C_{1-4}$alkyl-$SO_2$—, amino, mono- or di($C_{1-4}$alkyl)amino, $C_{1-4}$alkylcarbonylamino, or —$O(CH_2CH_2O)_3CH_2CH_2O$—.

More preferably, Z is selected from norbornane, adamantane, phenyl or pyridyl optionally being substituted with at least one substituent, each substituent independently selected from halo, hydroxyl, =O, $C_{1-6}$alkyl, $C_{1-6}$alkyloxy, $C_{1-6}$alkyloxycarbonyl, $C_{1-6}$alkylcarbonyloxy, $C_{1-6}$alkylthio, polyhalo-$C_{1-6}$alkyl, polyhalo$C_{1-6}$alkyloxy, cyano, nitro, carboxyl, $C_{1-4}$alkyl-$SO_2$—, amino, mono- or di($C_{1-4}$alkyl)amino, $C_{1-4}$alkylcarbonylamino, or —$O(CH_2CH_2O)_3CH_2CH_2O$—.

Still more preferably, Z is selected from norbornane, adamantane, phenyl or pyridyl optionally being substituted with at least one substituent, each substituent independently selected from hydroxyl, $C_{1-6}$alkyl, —$O(CH_2CH_2O)_3CH_2CH_2O$— or =O.

Preferably, the compound is selected from:

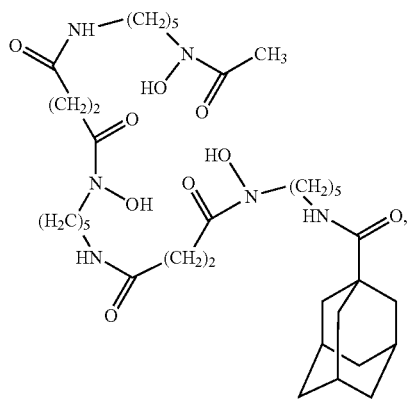

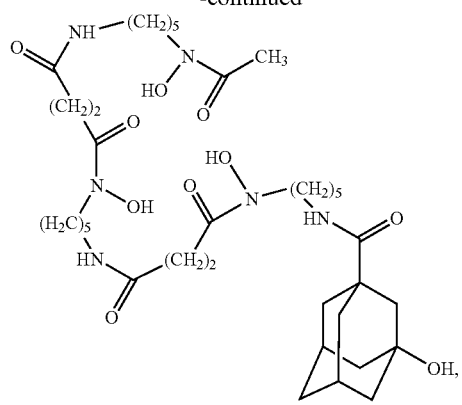
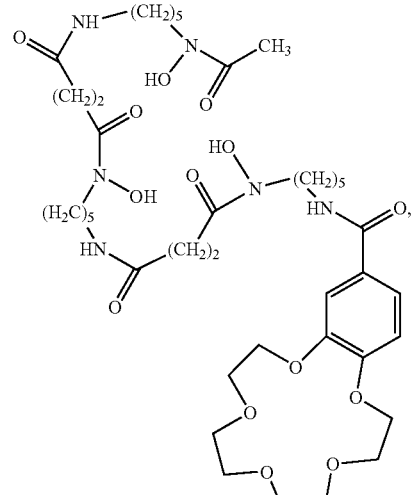
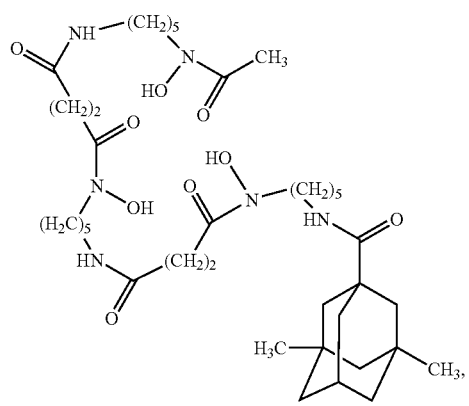
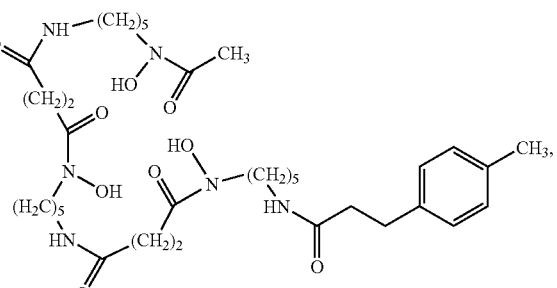
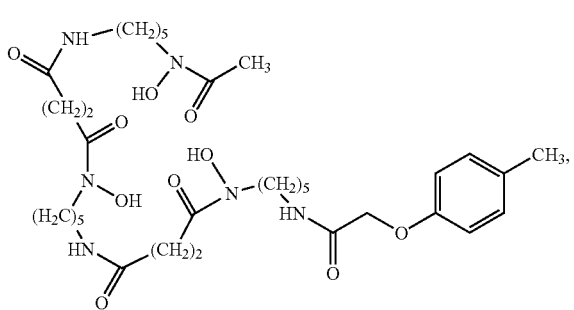
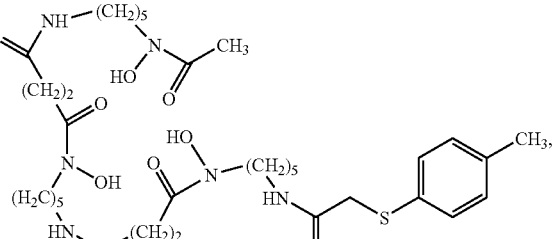
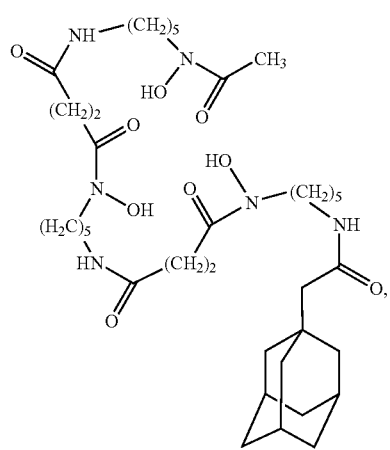
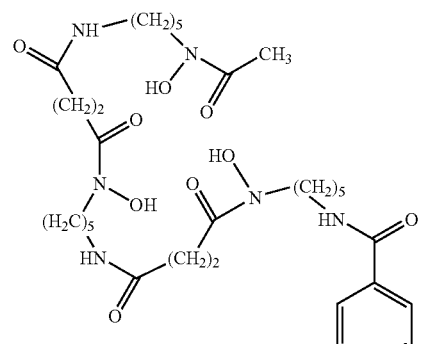
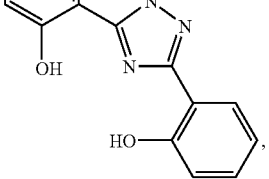

21
-continued
22
-continued
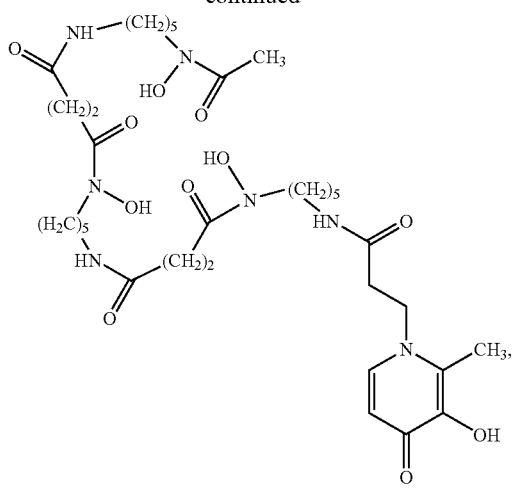
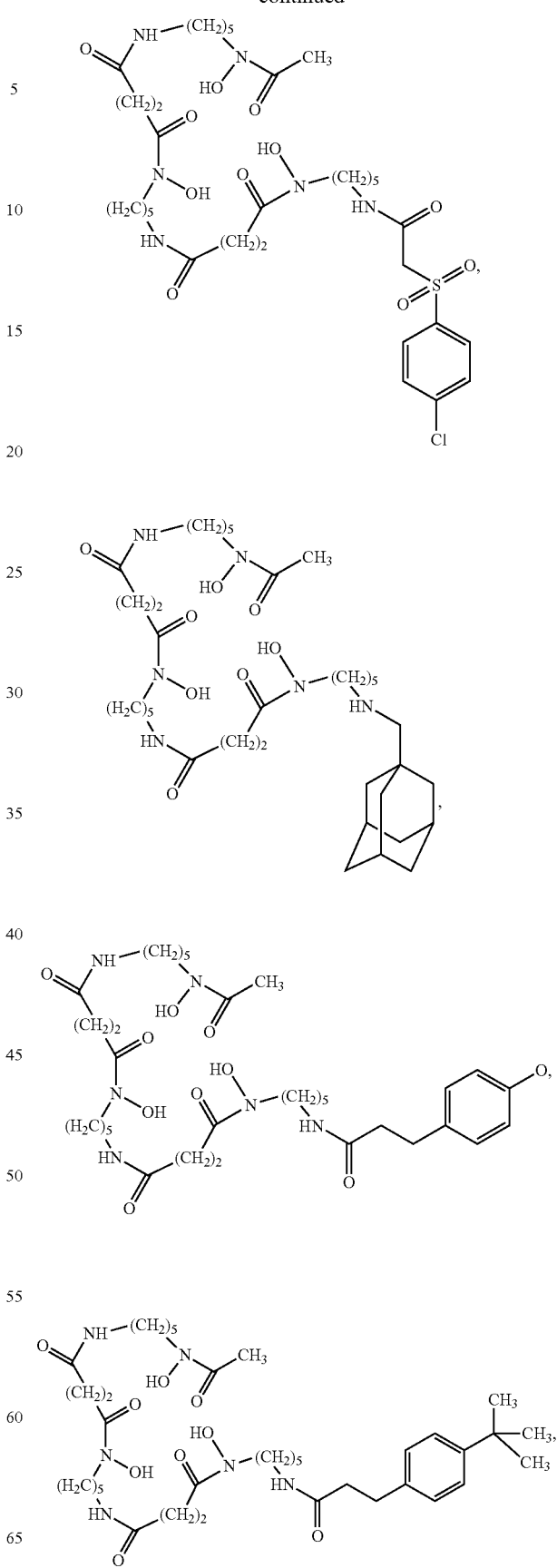

23
-continued
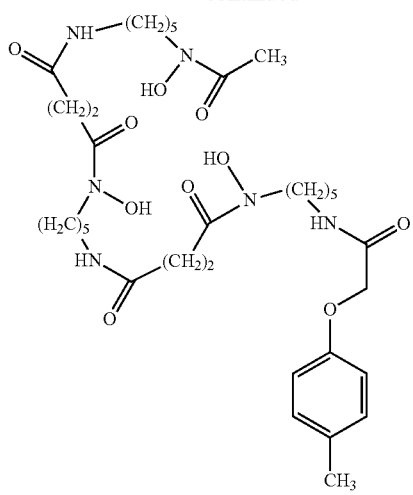
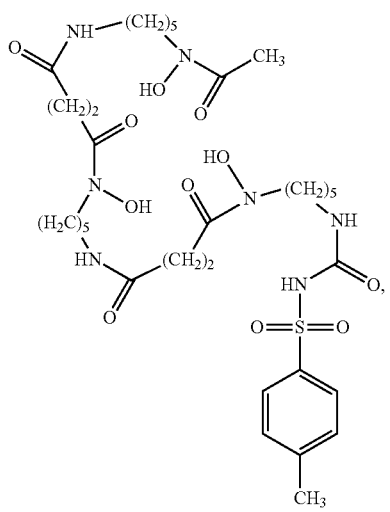
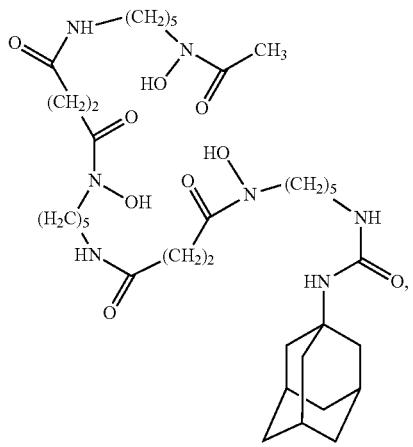
24
-continued
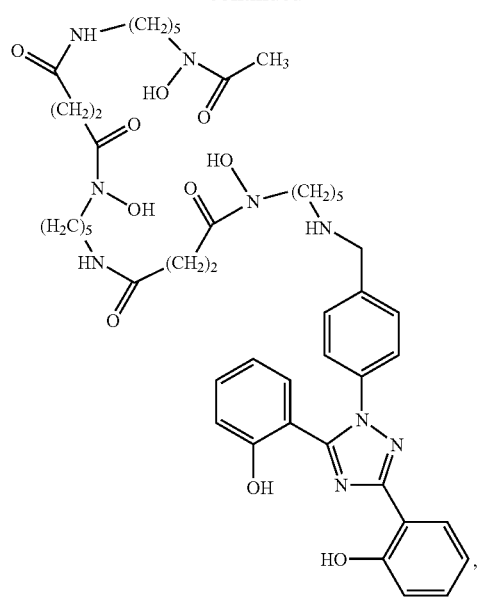
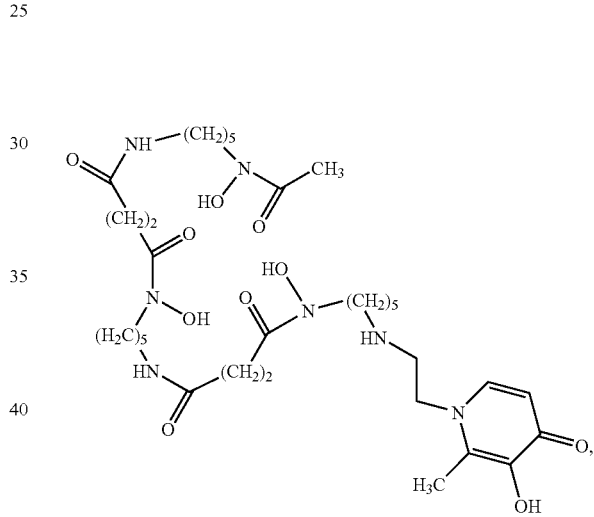
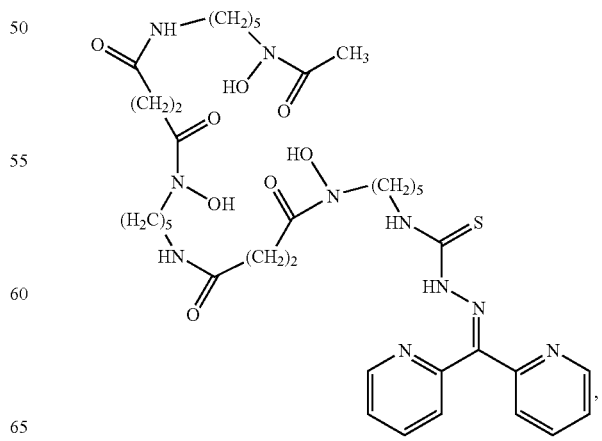

25
-continued
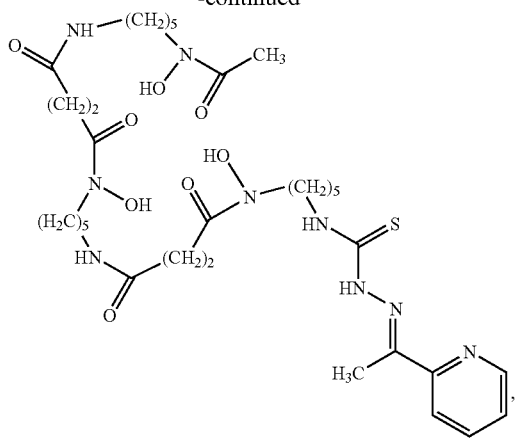
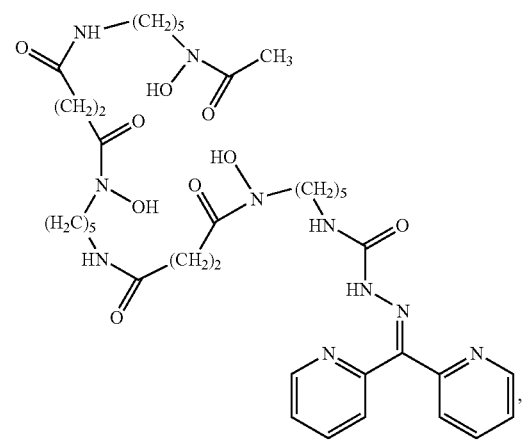
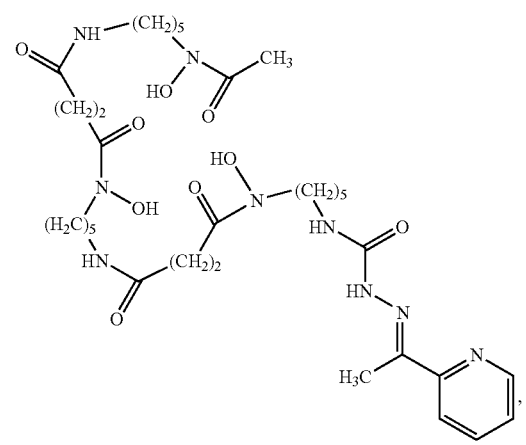
26
-continued
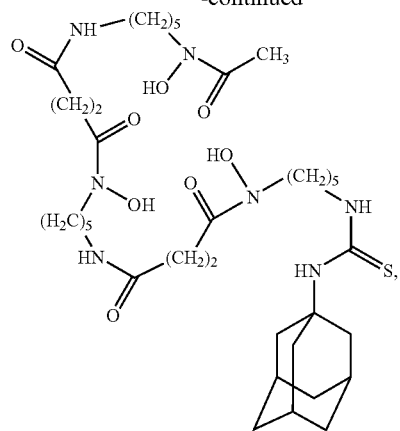
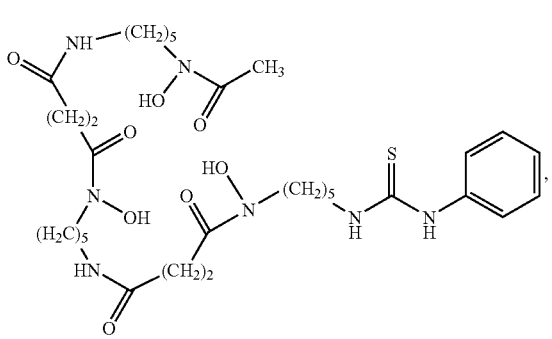
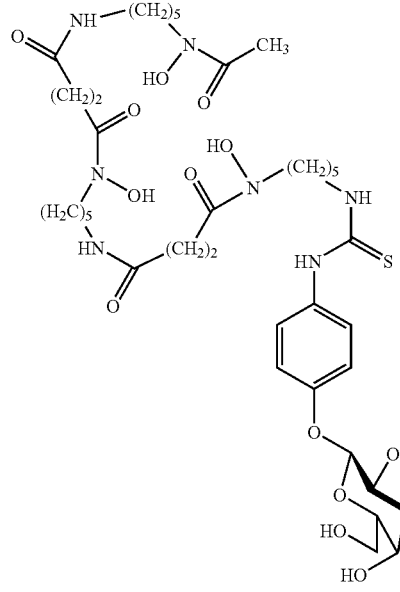

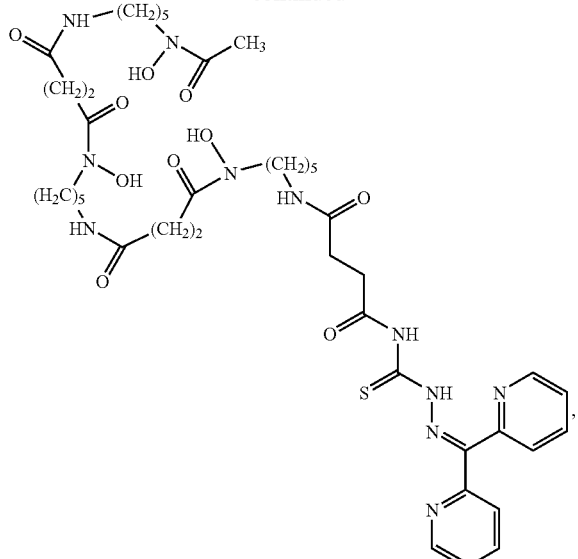
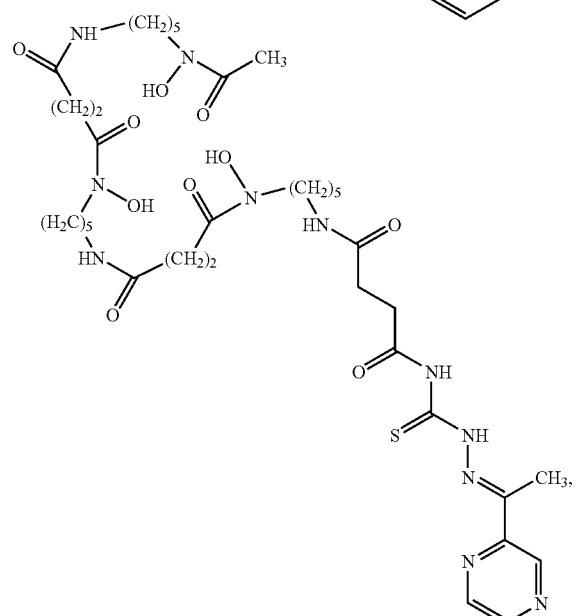
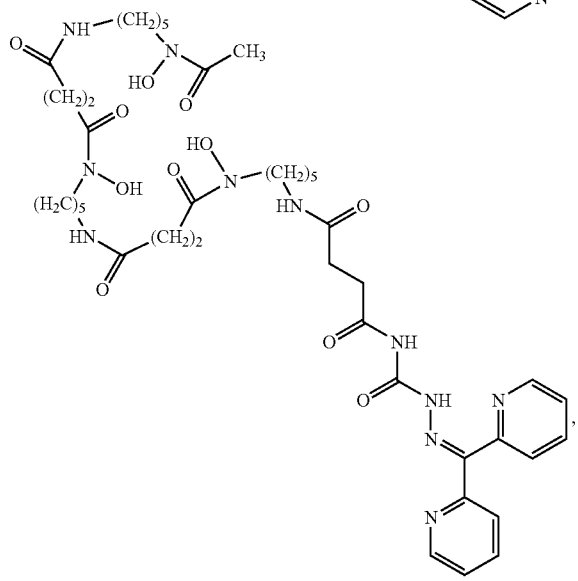

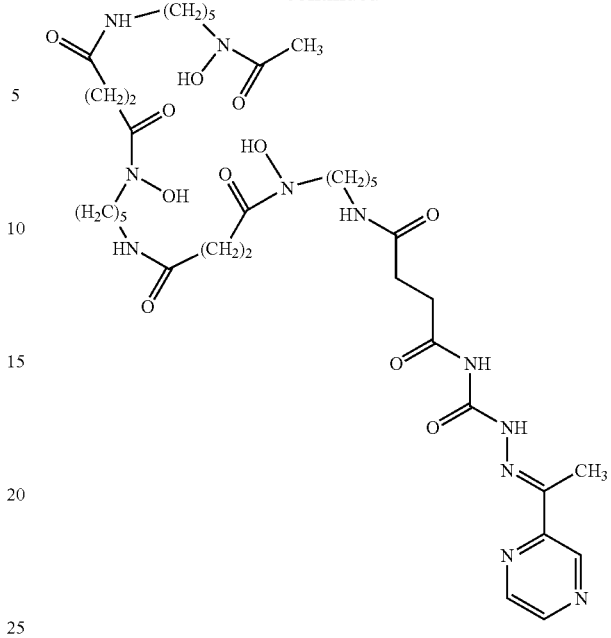

or a pharmaceutically acceptable salt thereof, together with a pharmaceutically acceptable excipient, diluent or carrier.

Preferably, the pharmaceutical composition according to the invention may comprise one or more compounds of Formula I. Optionally, the pharmaceutical composition may also include one or more additional pharmaceutically active agents in addition to the one or more compounds of Formula I.

In a preferred embodiment the pharmaceutical composition may be administered in combination with one or more additional agents effective for controlling iron overload, such as deferoxamine mesylate.

The pharmaceutical compositions of the present invention may be administered subcutaneously or intravenously. However, it is preferable to administer the composition orally. In particular, the conjugates, derivatives and analogues of the present invention exhibit increased hydrophobicity, relative to Desferal, thereby providing the potential for oral administration of compounds for the treatment of iron-overload. It is contemplated that the conjugates, derivatives and analogues of the present invention may exhibit an increased cardioprotective response relative to desferrioxamine.

This is advantageous as desferrioxamine can only be administered subcutaneously or intravenously. Further advantages of the present invention will be apparent to the person skilled in the relevant art. For example, a lower dose may be required, and/or fewer administrations may be required. Additionally there may be reduced side effects, reduced toxicity, and improved compliance with a treatment regime.

A pharmaceutically acceptable diluent may be sterile water or saline.

Acceptable carriers for use in the invention include saline or buffers such as phosphate, citrate, acetate, and other organic acids; antioxidants including ascorbic acid; low molecular weight (e.g., less than about 10 residues) polypeptides; proteins, such as serum albumin (e.g., human serum albumin or bovine serum albumin), gelatin, and immunoglobulins; hydrophilic polymers such as polyvinylpyrrolidone; amino acids such as glycine, glutamine, asparagines, arginine, and lysine; monosaccharides, disaccharides, and other carbohydrates including glucose, mannose, maltose, and dextrins; chelating agents such as EDTA; sugar alcohols such as mannitol and sorbitol; salt-forming counterions such as sodium; and/or nonionic surfactants such as TWEEN™, PLURONICS™, and PEG. Optionally, the formulations include a pharmaceutically acceptable salt, such as sodium chloride at about physiological concentrations. Optionally, the formulations of the invention can contain a pharmaceutically acceptable preservative (e.g., benzyl alcohol, phenol, m-cresol, methylparaben, or propylparaben). Further, the active ingredients can be entrapped in microcapsule or sustained-release preparations can be prepared.

Procedures for the preparation of dosage unit forms are readily available to those skilled in the art from texts such as *Pharmaceutical Handbook. A Martindale Companion Volume*, ed. Ainley Wade, 19$^{th}$ edition, The Pharmaceutical Press London; *CRC Handbook of Chemistry and Physics*, ed. Robert C. Weast, Ph.D., CRC Press Inc.; *Goodman and Gilman's, The Pharmacological basis of Therapeutics*, 9$^{th}$ edition, McGraw Hill; *Remington, The Science and Practice of Pharmacy*, 19$^{th}$ edition, ed. Alfonso R. Gennaro, Mack Publishing Co., Easton, Pa.; and *Remington's Pharmaceutical Sciences*, 20$^{th}$ edition, ed. A. Gennaro, 2000, Lippincott, Williams & Wilkins, Philadelphia, Pa.

According to an eleventh aspect, the present invention provides a kit for the treatment of iron overload comprising one or more compounds according to the invention, or an amide biotin conjugate of formula I, together with instructions for use.

According to a twelfth aspect, the present invention provides a kit for the treatment of a primary or secondary iron dyshomeostasis disorder comprising one or more compounds according to the invention, or an amide biotin conjugate of formula I, together with instructions for use.

Preferably, the primary iron-overload disorder may be selected from Parkinson's disease, Alzheimer's disease, Huntington's disease, haemochromatosis, anaemia, β-thalassaemia, myelodysplastic syndrome, aceruloplasminaemia, Friedreich's ataxia and congenital atransferrinaemia.

The haemachromatosis may be selected from haemochromatosis type 1, haemochromatosis type 2A, haemochromatosis type 2B, haemochromatosis type 3, haemochromatosis type 4, neonatal haemochromatosis.

Preferably, the anaemia is selected from sickle cell anaemia or Diamond-Blackfan anaemia.

The secondary iron-overload disorder may be selected from dietary iron overload, long term haemodialysis, chronic liver disease, Hepatitis C infection, alcoholic cirrhosis of the liver, non-alcoholic steatohepatitis or porphyria cutanea tarda.

According to a thirteenth aspect, the present invention provides a kit for the treatment of cancer comprising one or more compounds according to the invention, or an amide biotin conjugate of formula I, together with instructions for use.

According to a fourteenth aspect, the present invention provides a kit for the treatment of malaria comprising one or more compounds according to the invention, or an amide biotin conjugate of formula I, together with instructions for use.

According to a fifteenth aspect, the present invention provides a kit for the treatment of a fungal infection comprising one or more compounds according to the invention, or an amide biotin conjugate of formula I, together with instructions for use.

According to a sixteenth aspect, the present invention provides a method for reducing iron-overload in a mammal in need thereof, comprising administering to said mammal an effective amount of one or more compounds according to the invention, or an amide biotin conjugate of formula I.

According to a seventeenth aspect, the present invention provides use of an effective amount of one or more compounds according to the invention, or an amide biotin conjugate of formula I, in the preparation or manufacture of a medicament for reducing iron-overload in a mammal.

Advantageously, the present invention further includes a new drug design strategy for the treatment of iron overload disease in humans. In particular, conjugates, derivatives and analogues of the drug desferrioxamine (DFOB; Compound I—see FIGS. 1, 2 and 6) may be prepared by chemically modifying a primary amine of desferrioxamine via peptide coupling techniques.

The present Applicant has found that the conjugates, derivatives and analogues prepared and reported herein display markedly increased lipophilicity and similar or improved iron binding properties to desferrioxamine. Without wishing to be bound by any particular theory, the present Applicants expect that this may be due to the fact that the conjugates, derivatives and analogues of the present invention are uncharged. Further, it is also contemplated that the Fe(III) binding properties of the new drug conjugates, derivatives and analogues reported herein will not be affected, since no chemistry is taking place at the hydroxamate functional groups (i.e. the Fe(III) binding moieties).

More advantageously, the present invention provides for the conjugation of abiological chelates that mimic deferasirox (ICL670; Compound II—see FIG. 5) and deferiprone (L1; Compound III—see FIG. 5); these abiological chelates may be used in some patients who are not able to take Desferal™. Additionally, bifunctional adducts of desferrioxamine are provided in which Fe(III) binding can occur at both 'ends' of the molecule (see FIG. 21).

Exemplary conjugates of the present invention comprise inter alia molecules: IV, V, VI, VII and XII (see FIGS. 7 and 8). Conjugates IV, V, VI, VII and XII have been synthetically prepared and characterised by mass spectroscopy (MS).

More recent treatments for iron-overload disease involve combination therapy using a combination of DFOB and deferiprone (L1; Compound III).

Accordingly, a further embodiment of the invention provides a conjugate of DFOB and an analogue of L1 (Compounds XII—see FIG. 8) in which L1 is linked via an amide (Compound XII) or secondary amine bond.

The iron binding capacity of the compounds is not affected, as determined from electronic absorption spectroscopy.

One particular advantage of the compounds of the present invention relates to the protection of their N-terminus, which it is thought provides a relatively longer half-life before metabolites of the compounds are formed (in particular, Metabolite D is thought to be responsible for some of the toxic effects of desferrioxamine seen in the literature).

It is another advantage of the present invention that the compounds are more resistant to in vivo enzymatic degradation. Without wishing to be bound to any particular theory, it is thought that the coordination complex may be more resilient to enzymatic degradation, and therefore the compounds according to the invention possess a greater half-life than the linear structure of desferrioxamine.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Other than in the operating examples, or where otherwise indicated, all numbers expressing quantities of ingredients or reaction conditions used herein are to be understood as modified in all instances by the term "about". The examples are not intended to limit the scope of the invention. In what follows, or where otherwise indicated, "%" will mean "weight %", "ratio" will mean "weight ratio" and "parts" will mean "weight parts".

Although the invention has been described with reference to specific examples, it will be appreciated by those skilled in the art that the invention may be embodied in many other forms. In particular features of any one of the various described examples may be provided in any combination in any of the other described examples.

BRIEF DESCRIPTION OF THE DRAWINGS

Preferred embodiments of the invention will now be described, by way of example only, with reference to the accompanying drawings in which.

EXAMPLE 1

Synthesis of Compounds

Reagents

The following chemicals and solvents were obtained from Sigma-Aldrich: 1-adamantanecarboxylic acid (>99%), biotin, benzo-15-crown-5-4-carboxylic acid, 4-methylphenoxyacetic acid, desferrioxamine B mesylate (DFOB) (95%), N-(3-dimethylaminopropyl)-N'-ethylcarbodiimide.HCl (EDC) (protein sequence grade), N-hydroxysuccinimide (NHS) (98%), sodium hydroxide (NaOH) (reagent grade), iron(III) perchlorate hydrate (chloride <0.1%), and gallium (III) nitrate hydrate (99.9%), dimethylformamide (DMF) (biotech grate), acetonitrile (ACN) (biotech grade). Methanol (MeOH) (99%) was obtained from Mallinckrodt Chemicals. All chemicals and solvents were used as received.

NHS-Activation of Ligands

Figure 1:
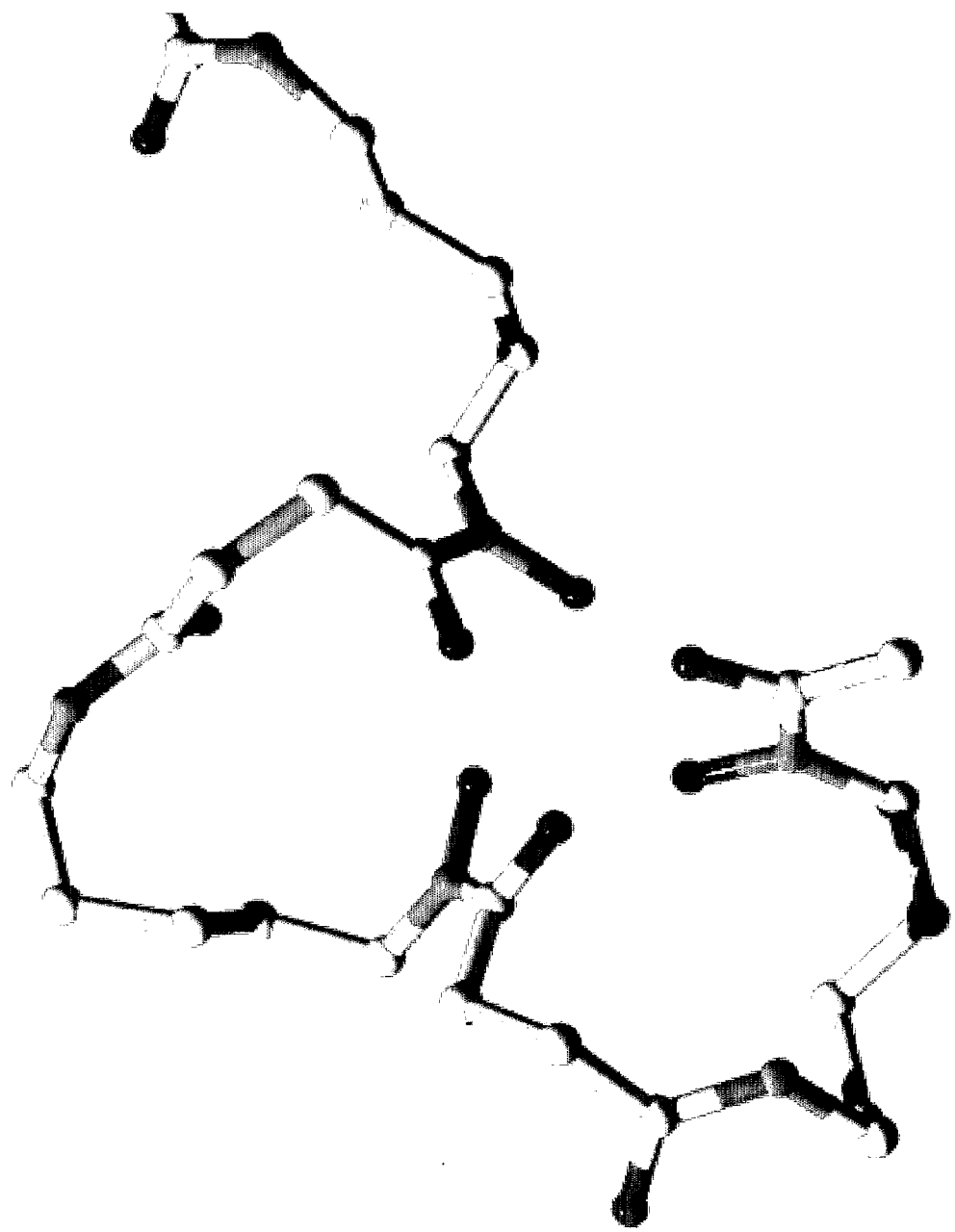
FIG. 1 is a ball and stick model of desferrioxamine B (DFOB)
Figure 2:
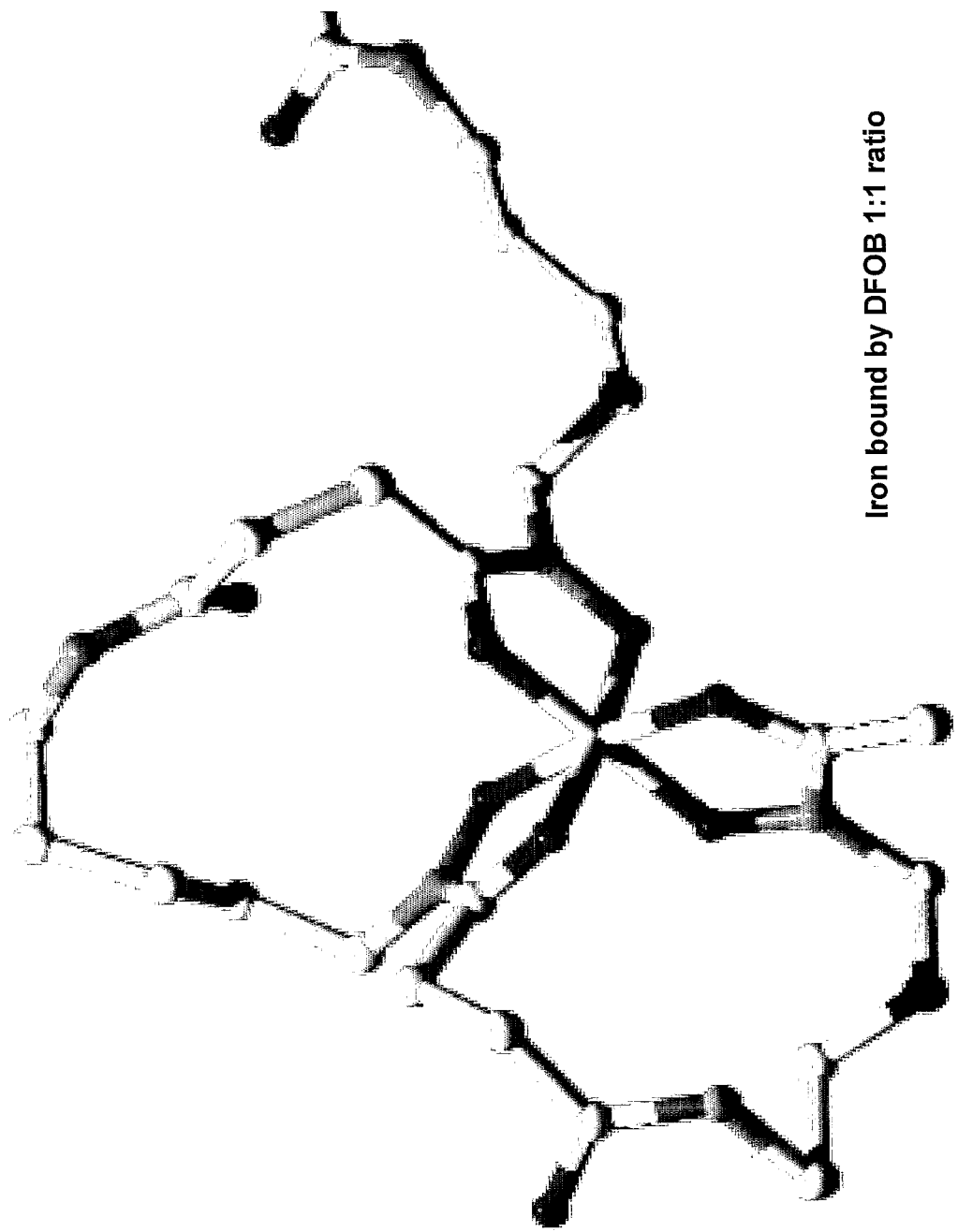
FIG. 2 is a view similar to FIG. 1 but showing DFOB bound in a 1:1 ratio to ferric iron.
Figure 3:
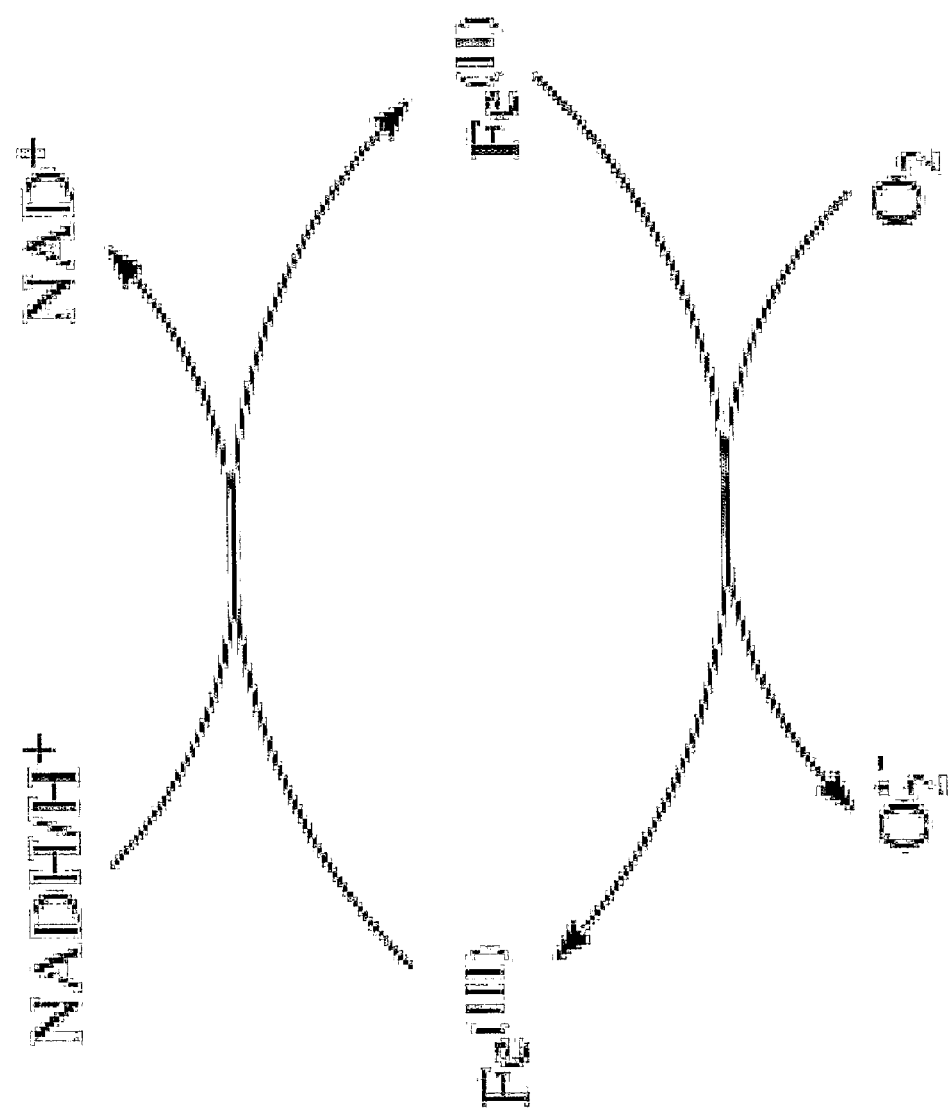
FIG. 3 is a schematic of a cellular process generating damaging free radicals via redox cycling activity.
Figure 4:
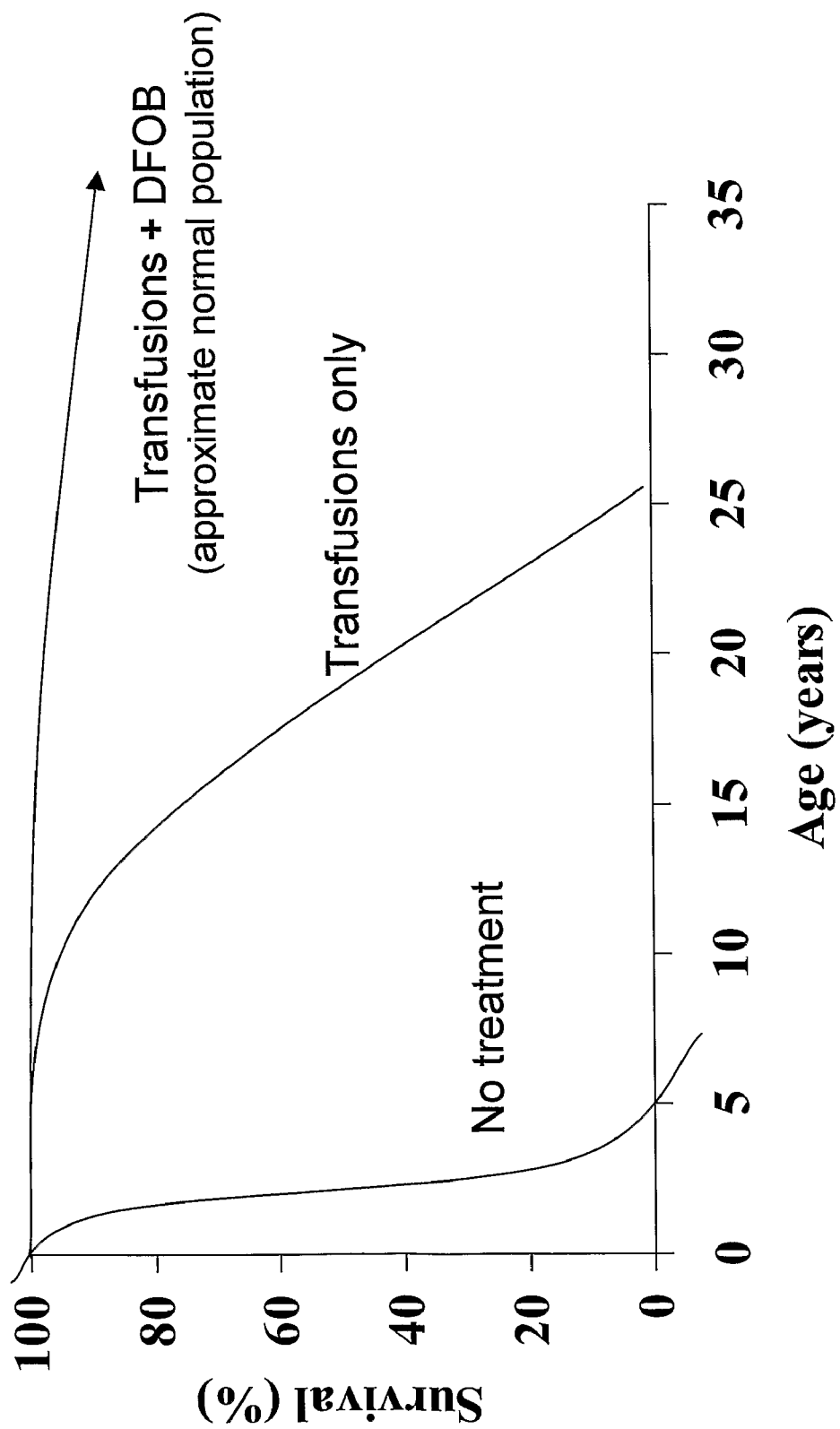
FIG. 4 is a graph of survival curves for patients with severe thalassemia syndromes.
Figure 5:
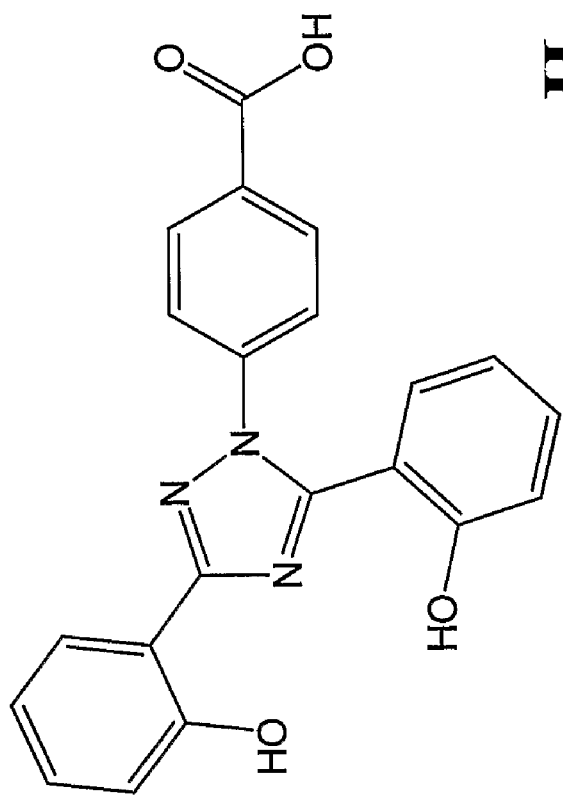
FIG. 5 shows the prior art chelators L1 (deferiprone) and ICL670 (deferasirox)
Figure 5:
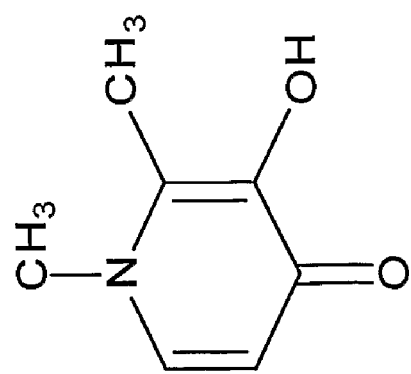
Figure 6:
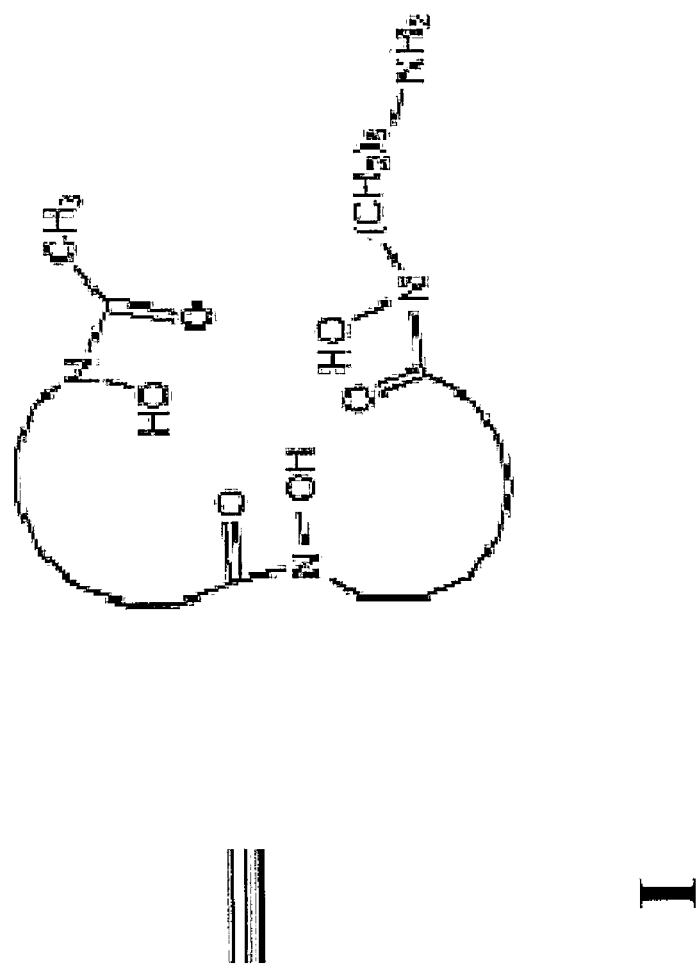
FIG. 6 shows a simplified chemical structure of desferrioxamine (Compound I)
Figure 6:
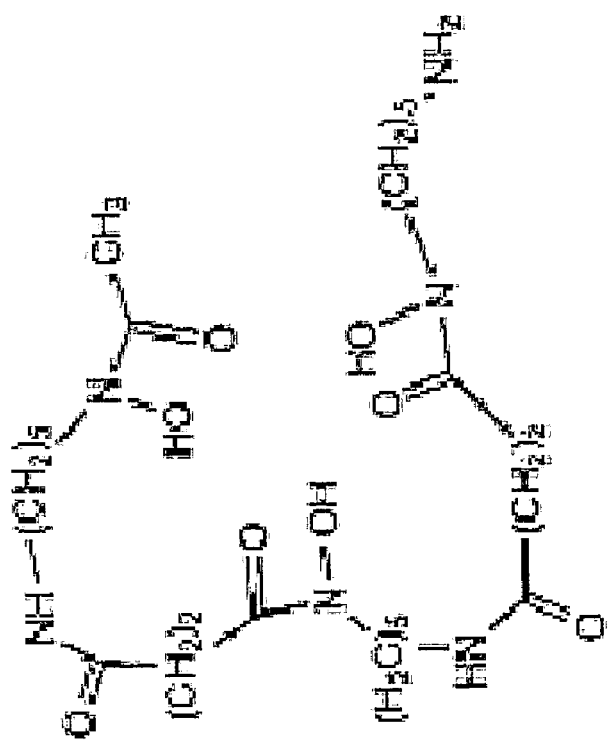
Figure 7:
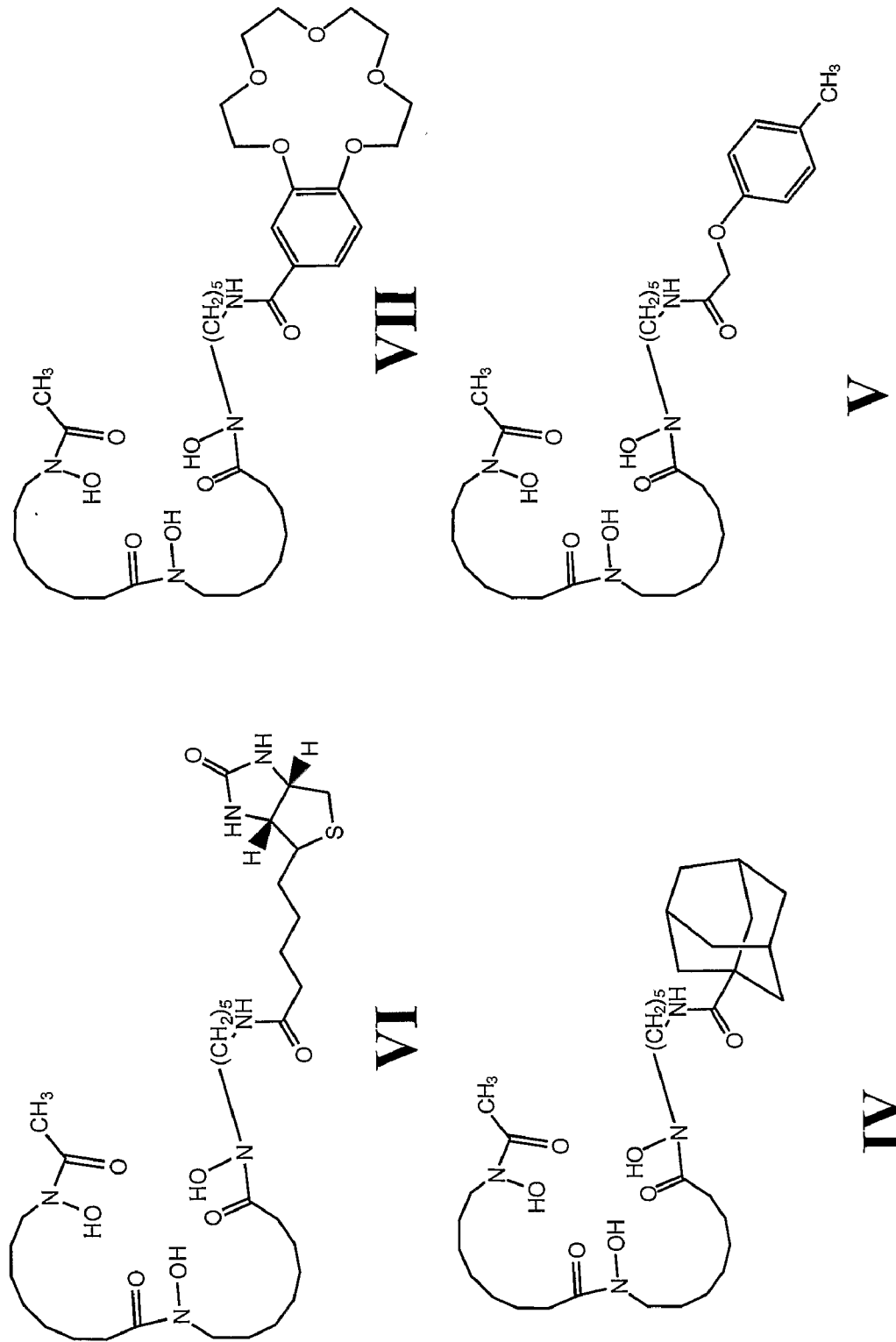
FIGS. 7 and 8 show desferrioxamine conjugates according to the present invention.
Figure 8:
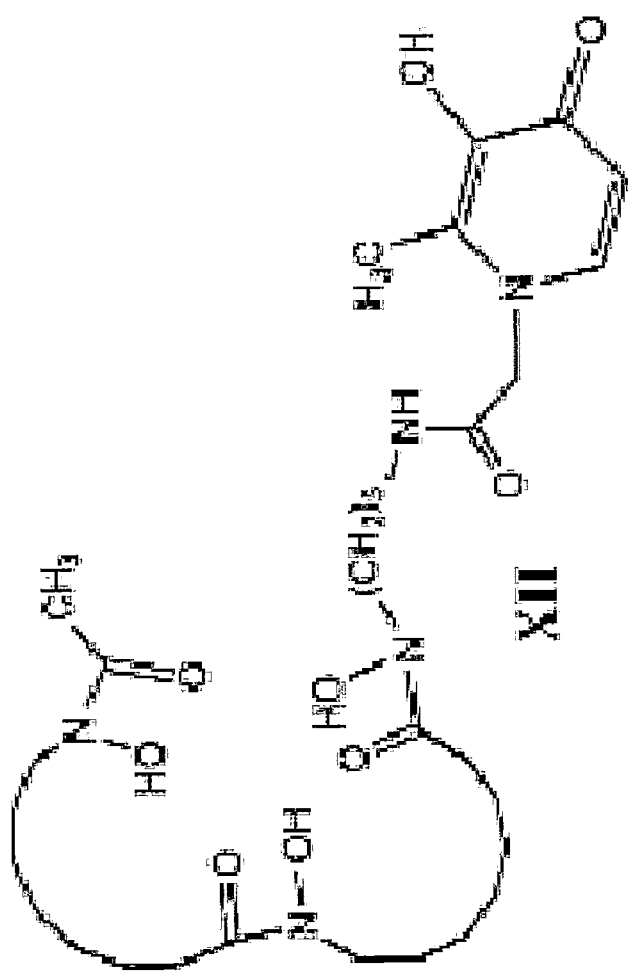
Figure 8:
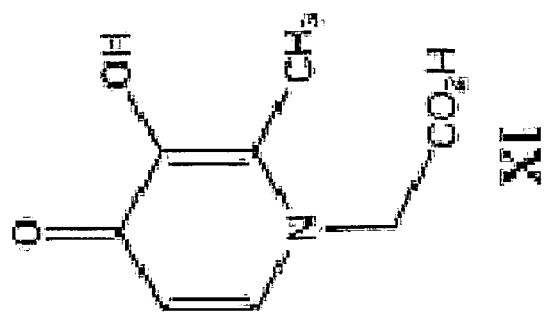
Figure 9:
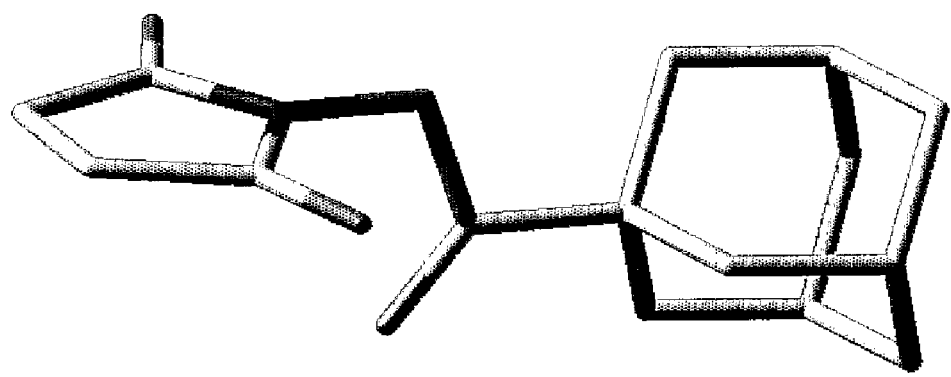
FIG. 9 is a stick model of N-[(1-adamantylcarbonyl)oxy]-succinimide (NHS-adamantane)
Figure 10:
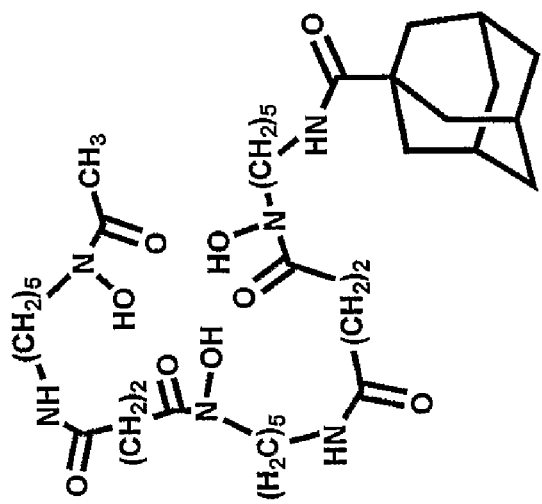
FIG. 10 shows electrospray ionisation mass spectrometry (ESI-MS) (positive ion mode) of adamantane-desferrioxamine B (Desferadax: $C_{36}H_{62}N_6O_9$; $M_r=722.92$ g mol$^{-1}$). Peaks at m/z 723.33 [M+H$^+$]$^+$ and m/z 745.53 [M+Na$^+$]$^+$.
Figure 10:
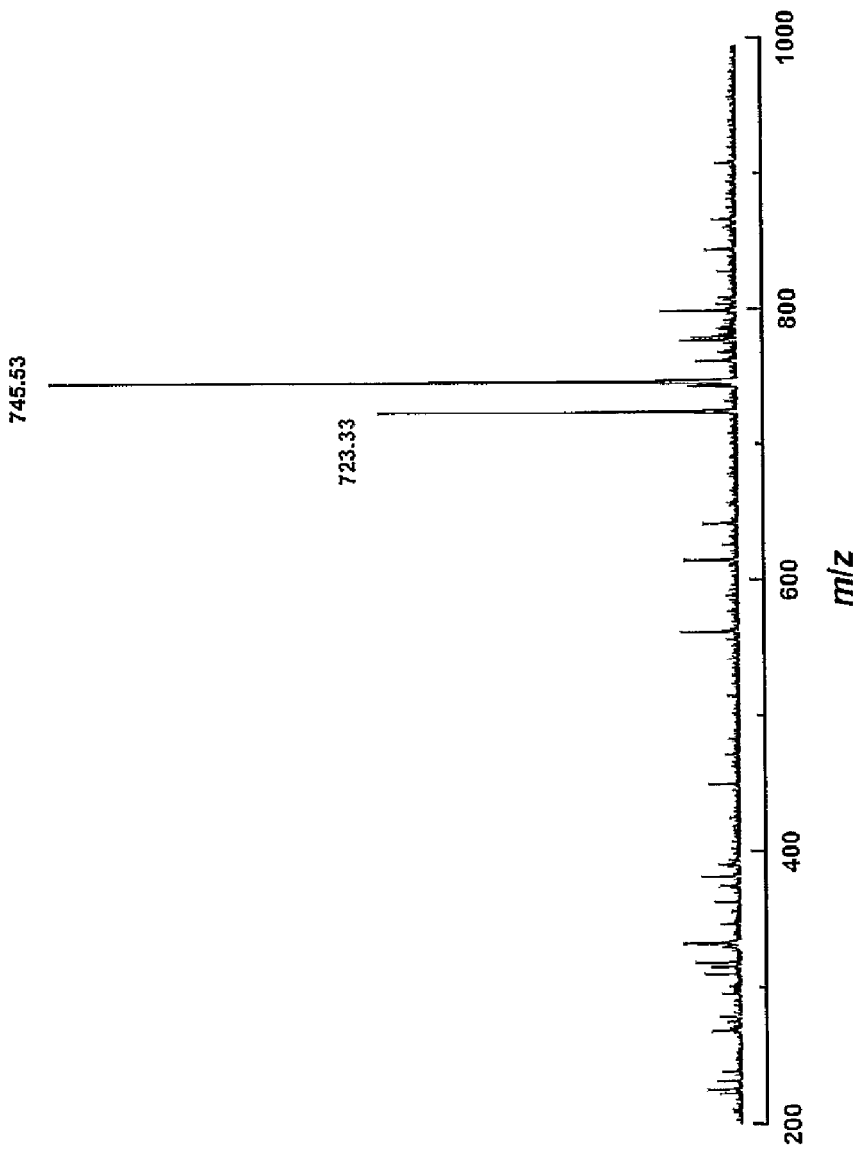
Figure 11:
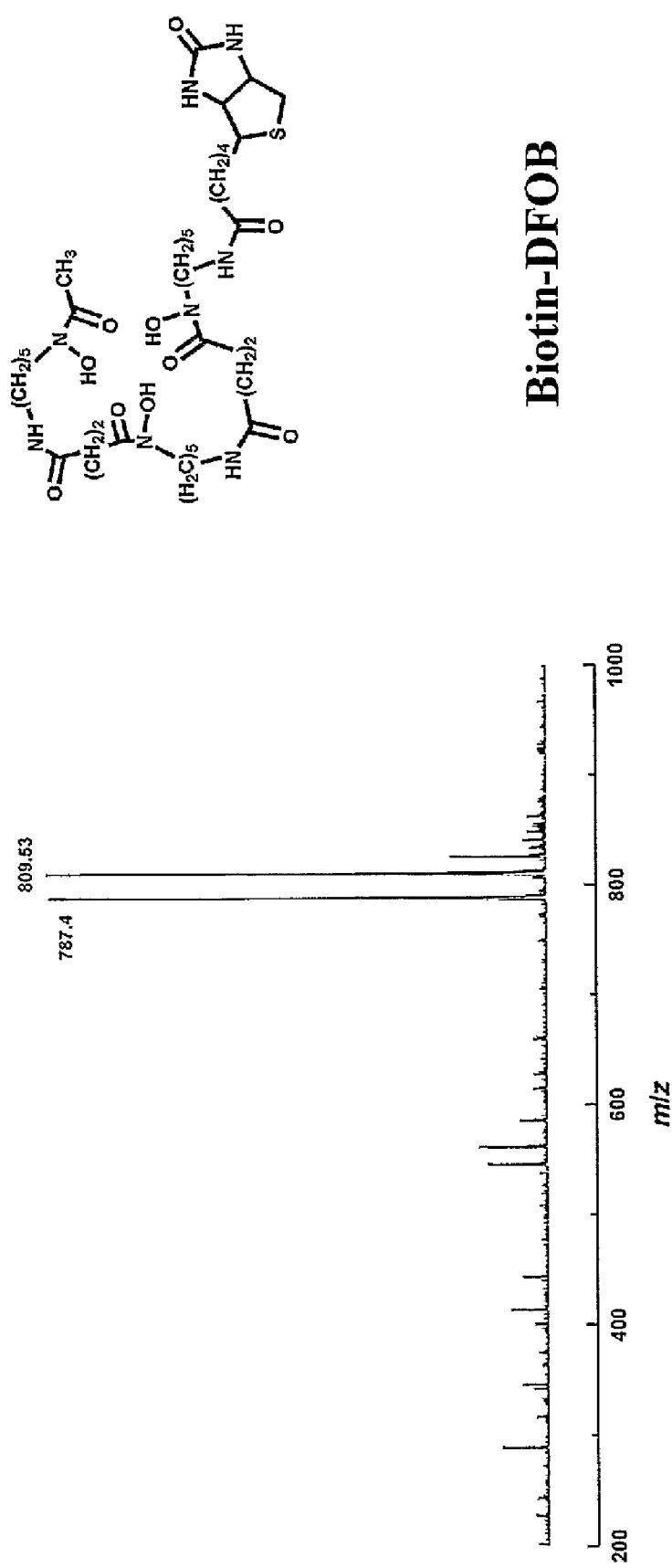
FIG. 11 shows ESI-MS (positive ion mode) of biotin-desferrioxamine B ($C_{35}H_{62}N_8O_{10}S$; $M_r=786.99$ g mol$^{-1}$). Peaks at m/z 787.40 [M+H$^+$]$^+$ and m/z 809.53 [M+Na$^+$]$^+$.
Figure 12:
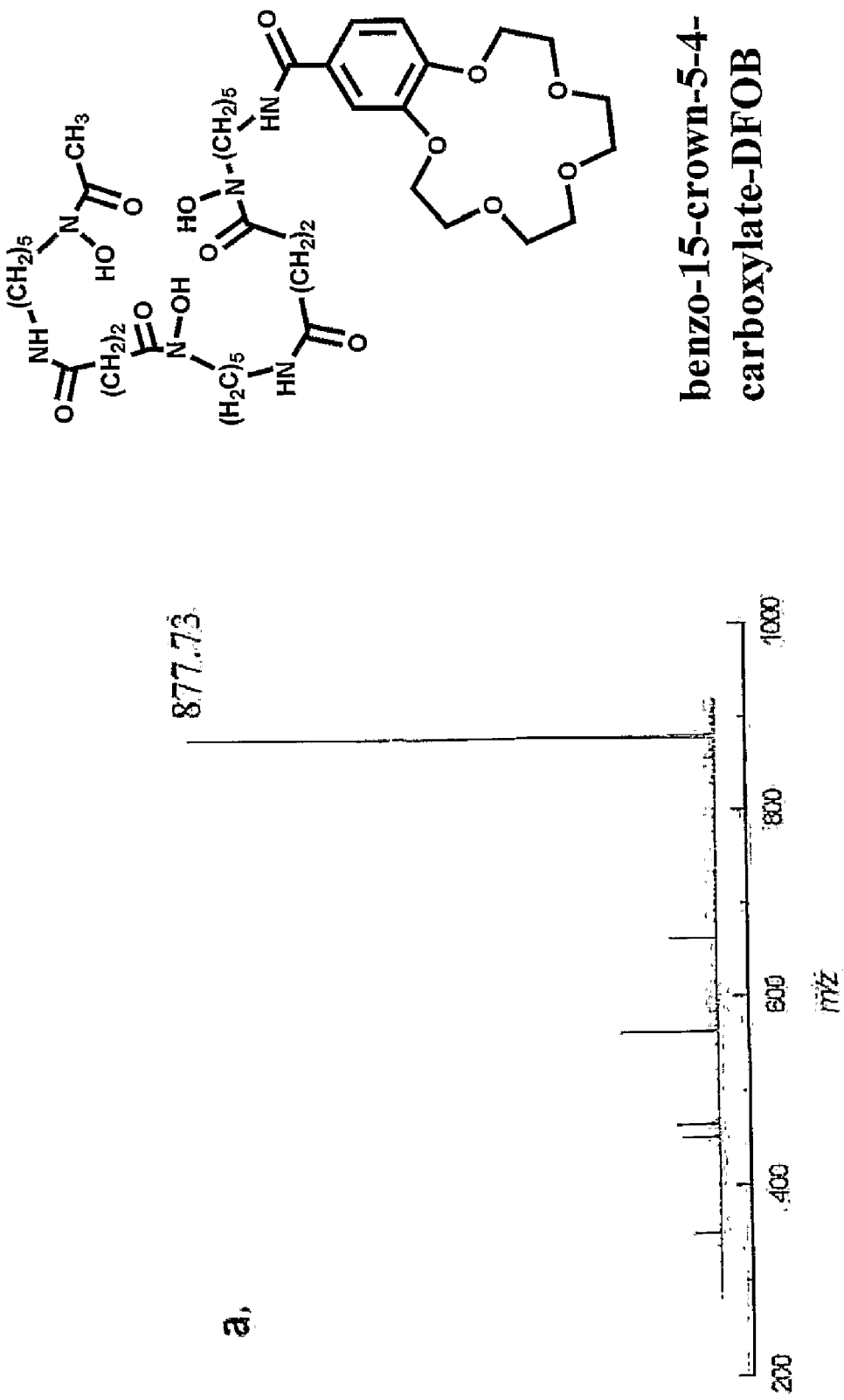
FIG. 12 shows ESI-MS (positive ion mode) of benzo-15-crown-5-4-carboxylate-desferrioxamine B ($C_{40}H_{66}N_6O_{14}$; $M_r=854.99$ g mol$^{-1}$). Peaks at m/z 877.73 [M+Na$^+$]$^+$.
Figure 13:
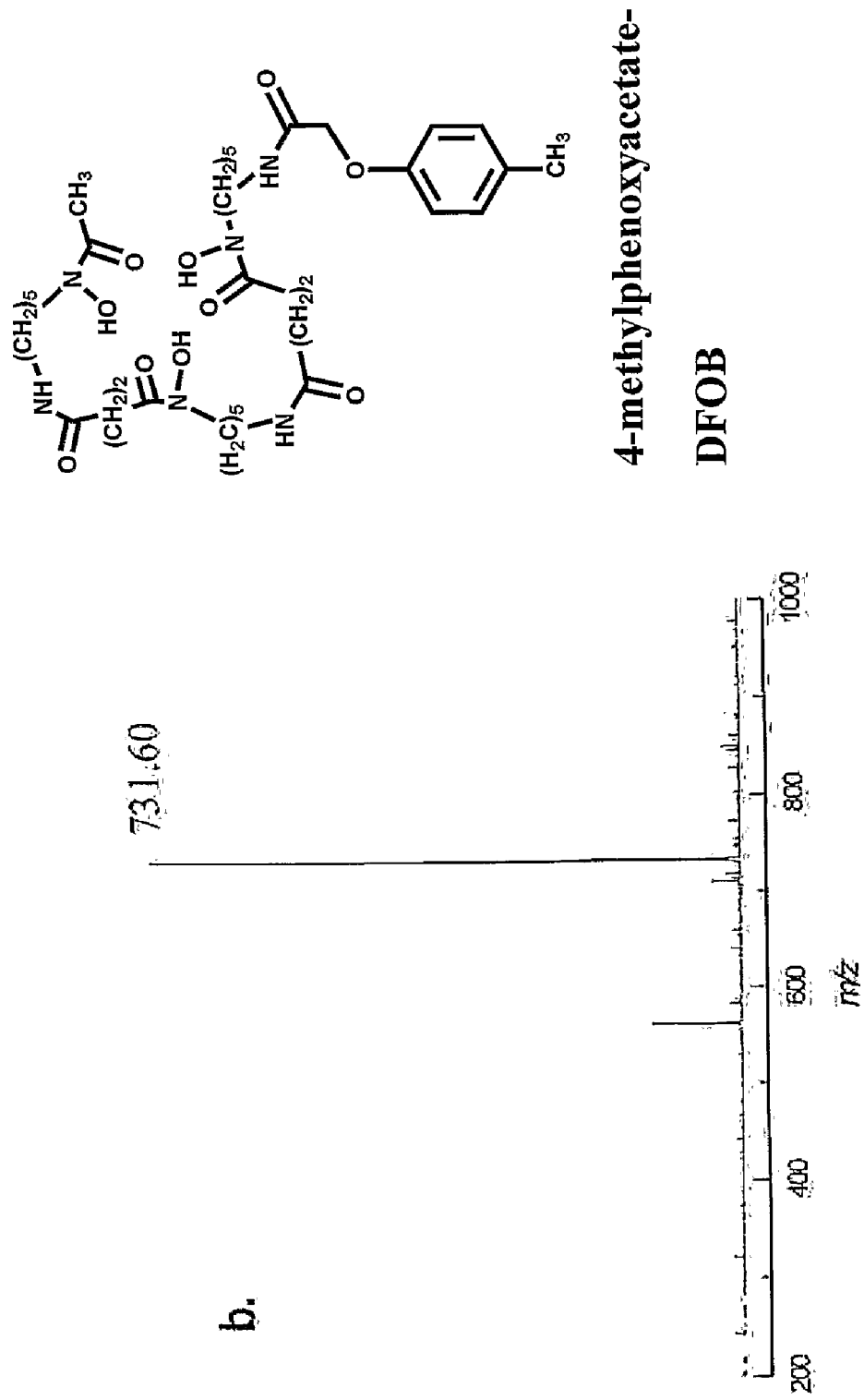
FIG. 13 shows ESI-MS (positive ion mode) of 4-methylphenoxyacetate-desferrioxamine B ($C_{34}H_{56}N_6O_{10}$; $M_r=708.85$ g mol$^{-1}$). Peaks at m/z 731.60 [M+Na$^+$]$^{30}$.
Figure 14:
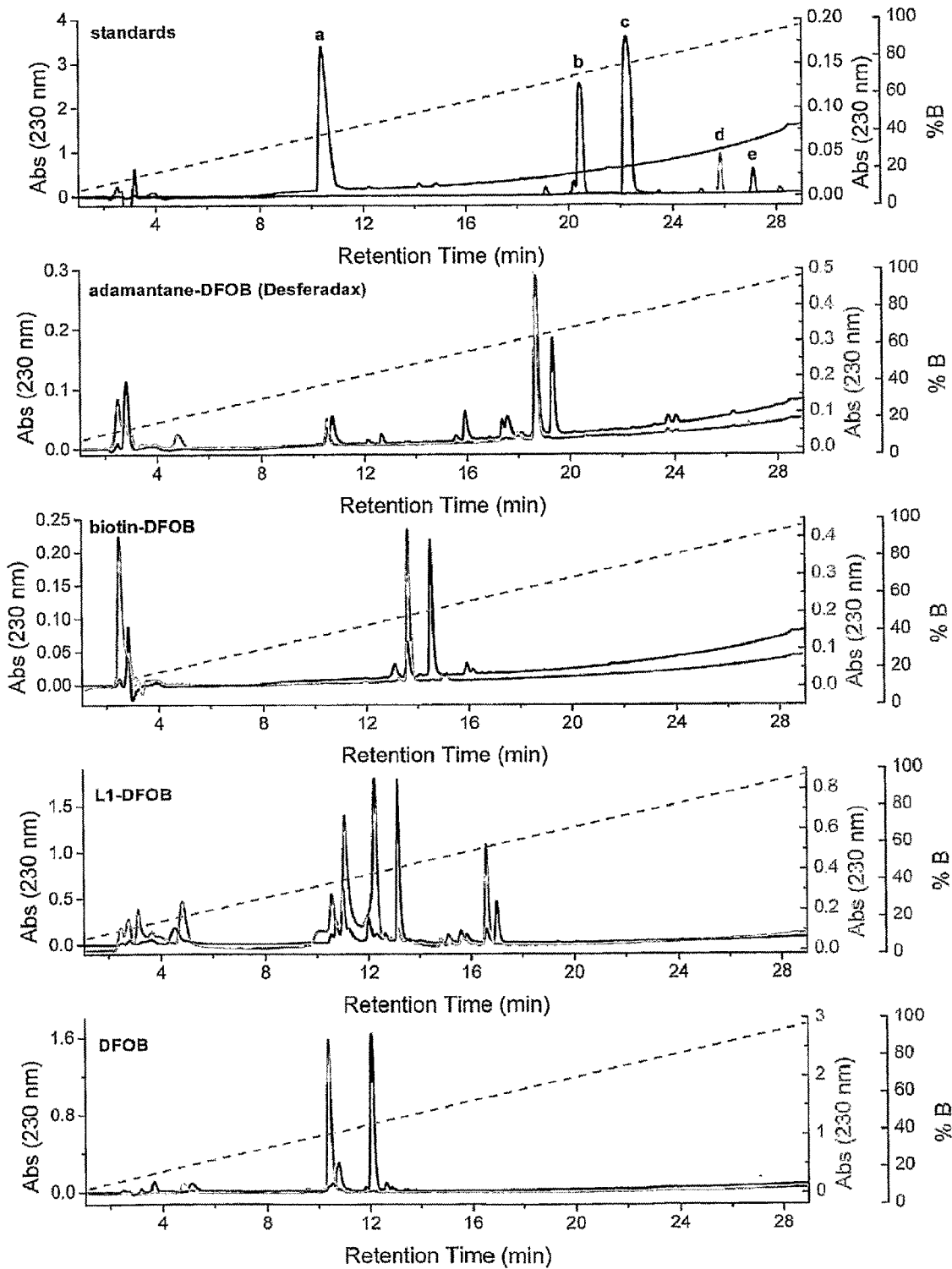
FIG. 14 shows reverse-phase high performance liquid chromatography (RP-HPLC) of DFOB, 3-hydroxy-1-acetate-2-methyl-4(1H)-pyridone-DFOB, biotin-DFOB and adamantane-desferrioxamine B. The standards (4-chloroaniline (a), 3-chlorophenol (b), α-naphthol (c), benzophenone (d), diphenylamine (e)) are shown in Table 2.
Figure 15:
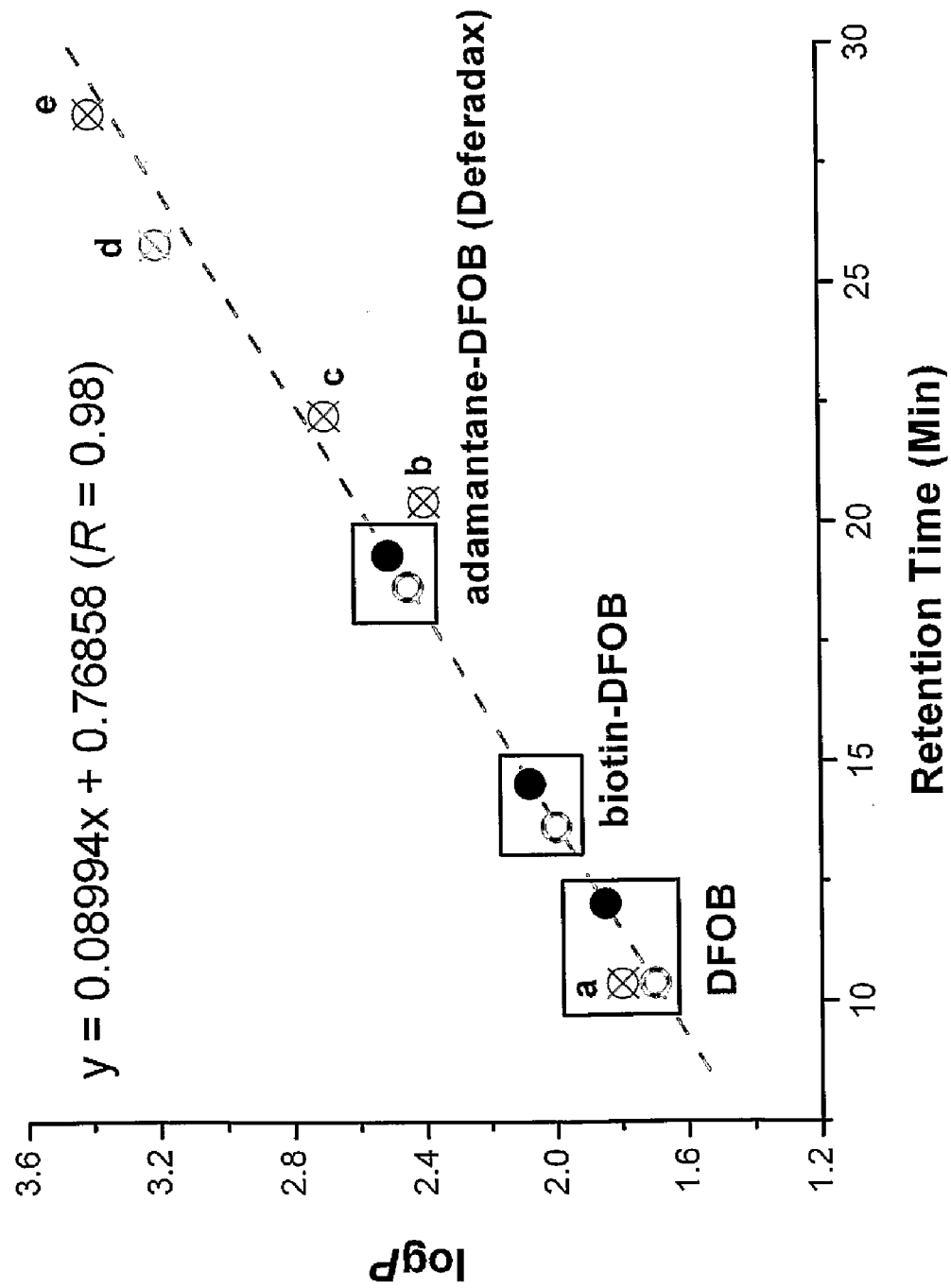
FIG. 15 shows a LogP correlation of standard compounds and DFOB, biotin-DFOB or adamantane-desferrioxamine B in the absence (open circles) and presence (closed circles) of Fe(III) (filled circles are iron-free compounds, open circles are Fe(III)-loaded compounds).

The following procedure was adapted from published methods [8]. An aliquot (2.55 mmol) of ligand (1-adamantanecarboxylic acid, biotin, benzo-15-crown-5-4-carboxylic acid or 4-methylphenoxyacetic acid) was dissolved in dimethylformamide (10 mL) N-Hydroxysuccinimide (294 mg, 2.55 mmol) and EDAC (387 mg, 2 mmol) were added with stirring to the mixture at room temperature and following dissolution, the clear solution was left overnight. The volume of the solution was reduced to 5 mL (Speedvac, 60° C., 40 min or via rotary evaporation). Water (~3 mL) was added to the solution which was then refrigerated at 4° C. overnight. The white precipitate that formed was isolated by filtration using a sintered glass funnel and the solid washed with water (~2 mL). Yields: NHS-adamantane (73.3%), NHS-biotin (80.6%), NHS-benzo-15-crown-5-4-carboxylate (87%), NHS-4-methylphenoxyacetate (57.8%). The purities of the NHS-activated adducts were confirmed by ESI-MS and $^1$H NMR spectroscopy; data were in agreement with available literature values for NHS-adamantane [9] and for NHS-biotin [10]. In the case of one of the syntheses of NHS-adamantane, crystals were grown from a 0.6 mM solution of the compound in ~50% aqueous ethanol (FIG. 15).

Synthesis of Adamantane-Desferrioxamine B (Desferadax)

NaOH (0.036 g, 0.90 mmol) and N-[(1-adamantylcarbonyl)oxy]-succinimide (NHS-adamantane, 0.25 g, 0.90 mmol) were dissolved in MeOH (14 mL, 40° C.). DFOB·mesylate (0.29 g, 0.447 mmol) was added with stirring and the solution left at 40° C. for 4 h. Alternatively, NaOH was added to DFOB mesylate prior to the addition of N-[(1-adamantylcarbonyl)oxy]-succinimide (NHS-adamantane) as described for related NHS-esters, below. The volume of the solution was reduced in vacuo until the solution was slightly cloudy at which point, an aliquot (5 mL) of water was added to the solution which resulted in the formation of a precipitate. The suspension was kept in a refrigerator (4° C.) overnight. The white precipitate was filtered and washed with small amounts of water and air dried. Yield: 0.298 g, 92%.

Synthesis of Biotin-DFOB, benzo-15-crown-5-4-carboxylate-DFOB and 4-methylphenoxyacetate-desferrioxamine B This method was modified from a published procedure [8]. Desferrioxamine B mesylate (0.293 mg, 0.447 mmol) and NaOH (18 mg, 0.447 mmol) were dissolved in MeOH (20 mL). An approximate 2-fold molar excess of the solid NHS-activated ligands (NHS-biotin, NHS-benzo-15-crown-5-4-carboxylate or NHS-4-methylphenoxyacetate) were added to the DFOB/NaOH solution and the mixtures were heated in a water bath at 55° C. for 4 h. The volumes of the solution were reduced via rotary evaporation (45° C., 30 min) until a precipitate formed. The products were filtered, washed with water (~2 mL) and dried overnight. Yields: biotin-DFOB (68%); benzo-15-crown-5-4-carboxylate-DFOB (74%), 4-methylphenoxyacetate-DFOB (71%).

Synthesis of 3-hydroxy-1-acetic acid-2-methyl-4 (1H)-pyridone (TpakG)

This compound was prepared using a literature procedure [11] and the integrity of the complex confirmed by $^1$H NMR spectroscopy and ESI-MS (positive ion): $[M+H^+]^+$=184.1, $[2M]^+$=366.8. Attempted syntheses of 3-hydroxy-1-acetate-2-methyl-4(1H)-pyridone-DFOB using NHS and dicyclohexylacarbodiimide (DCC) has produced a conjugate that is impure (refer HPLC). Ongoing experiments will couple 3-hydroxy-1-acetic acid-2-methyl-4(1H)-pyridone and DFOB using 1-hydroxybenzotriazole (HOBT) and diisopropylcarbodiimide (DIC) [12].

EXAMPLE 2

Characterisation of Compounds Using Electrospray Ionisation Mass Spectrometry (ESI-MS)

Figure 16:
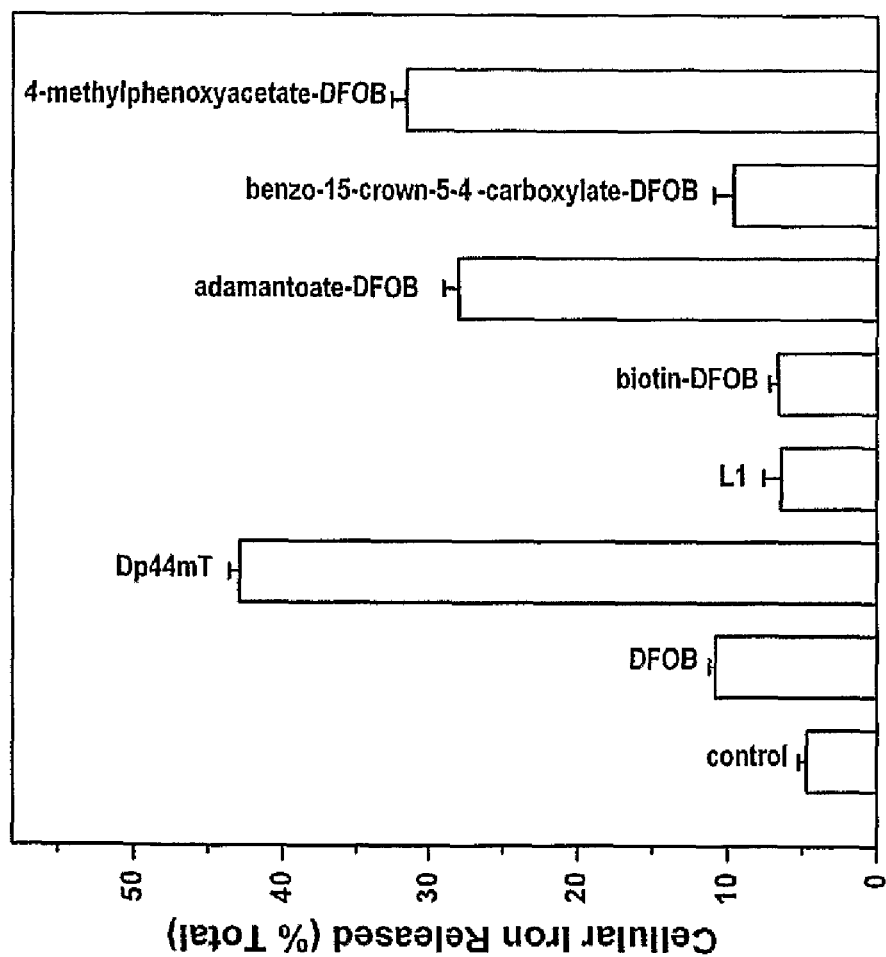
FIG. 16 shows efflux of $^{59}$Fe from $^{59}$Fe-prelabeled SK-N-MC cells (conducted as per literature procedures [13, 15, 16]) in the presence of control, DFOB, Dp44mT (di-2-pyridylketone-4,4,-dimethyl-3-thiosemicarbazone)[17], L1 (deferiprone), biotin-DFOB, adamantane-DFOB, benzo-15-crown-5-4-carboxylate-DFOB or 4-methylphenoxyacetate-DFOB.
Figure 17:
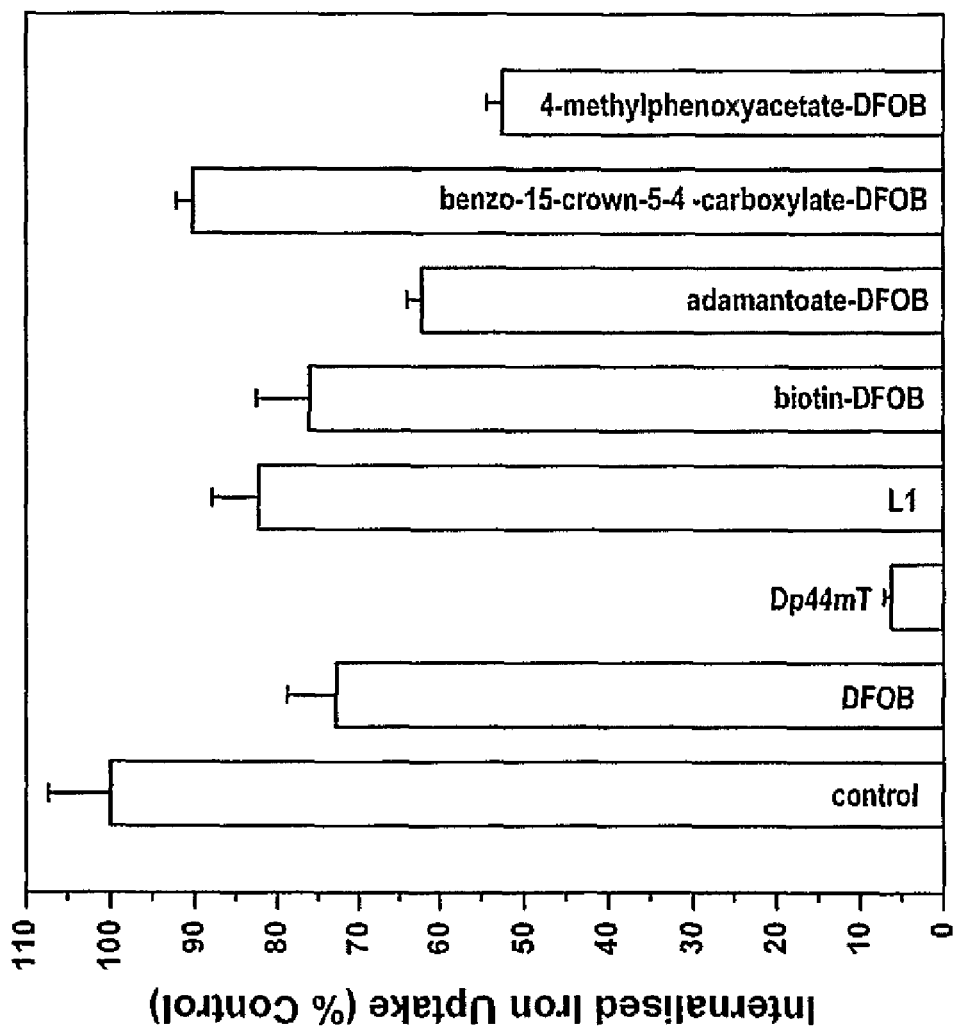
FIG. 17 shows $^{59}$Fe uptake into SK-N-MC cells from $^{59}$Fe-loaded transferrin (conducted as per literature procedures [18, 19]) in the presence of control, DFOB, Dp44mT (di-2-pyridylketone-4,4,-dimethyl-3-thiosemicarbazone)[17], L1 (deferiprone), biotin-DFOB, adamantane-DFOB, benzo-15-crown-5-4-carboxylate-DFOB or 4-methylphenoxyacetate-DFOB.
Figure 18:
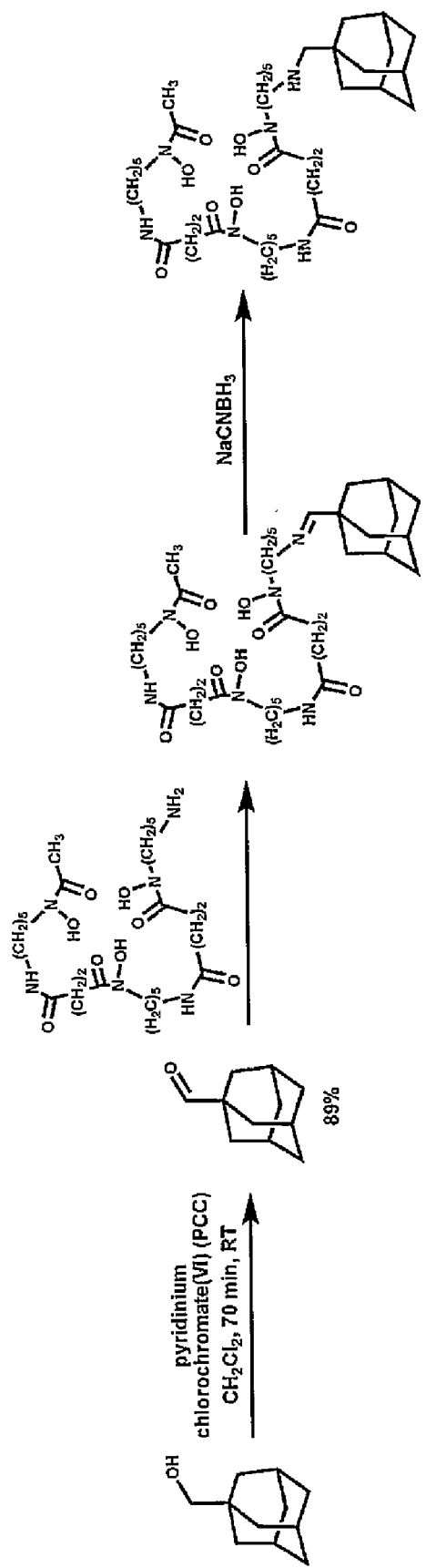
FIG. 18 shows the synthesis of secondary-amine-based adamantane-DFOB.
Figure 19:
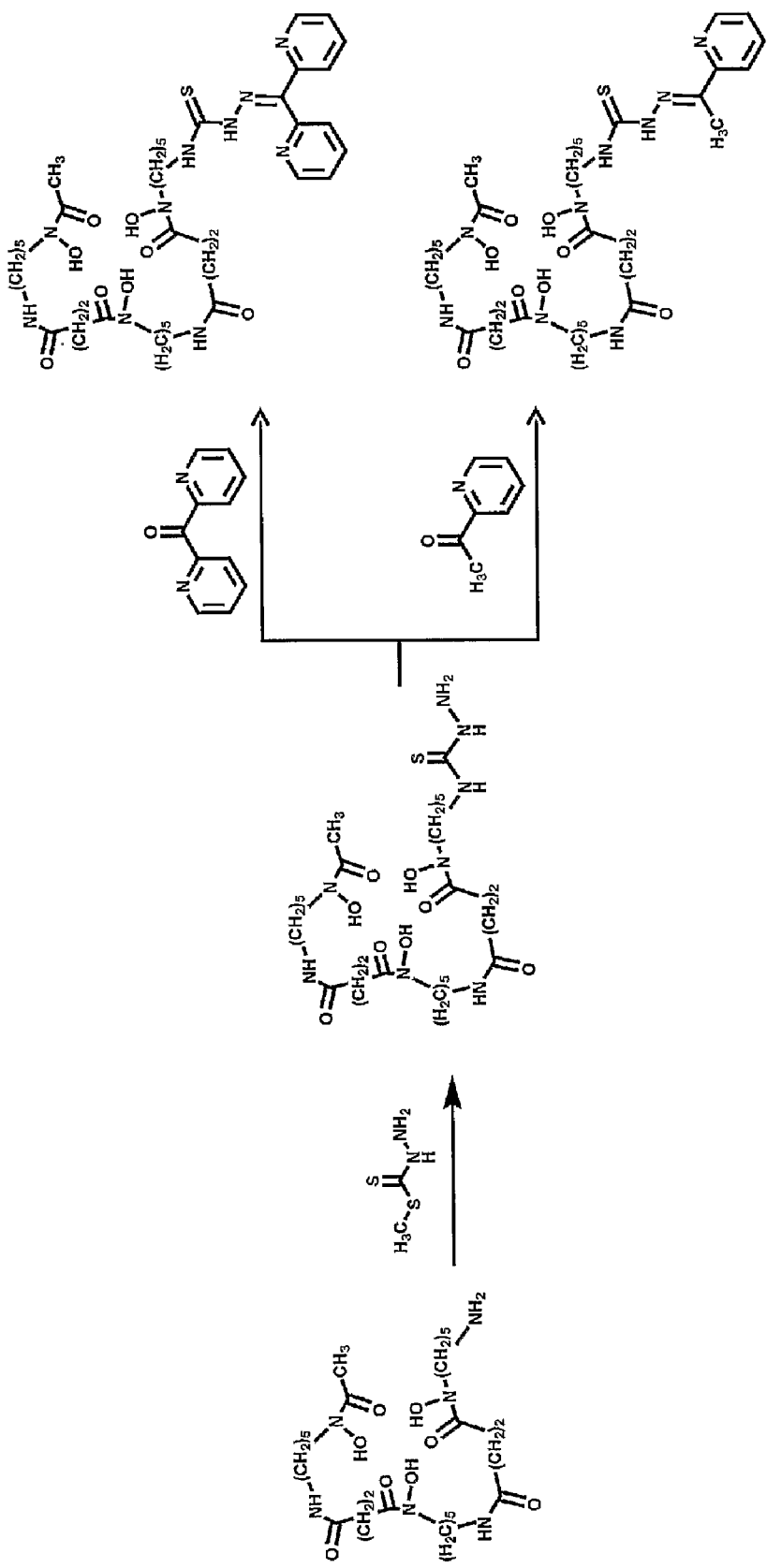
FIG. 19 shows the synthesis of thiosemicarbazone-based derivatives of DFOB.

The identity of the major products as adamantane-desferrioxamine B (Desferadax, 1) (FIG. 16), biotin-DFOB (FIG. 17), benzo-15-crown-5-4-carboxylate-DFOB (FIG. 18) and 4-methylphenoxyacetate-DFOB (FIG. 19) was confirmed by ESI-MS.

EXAMPLE 3

Reverse Phase High Pressure Liquid Chromatography (RP-HPLC) of Compounds

Figure 20:
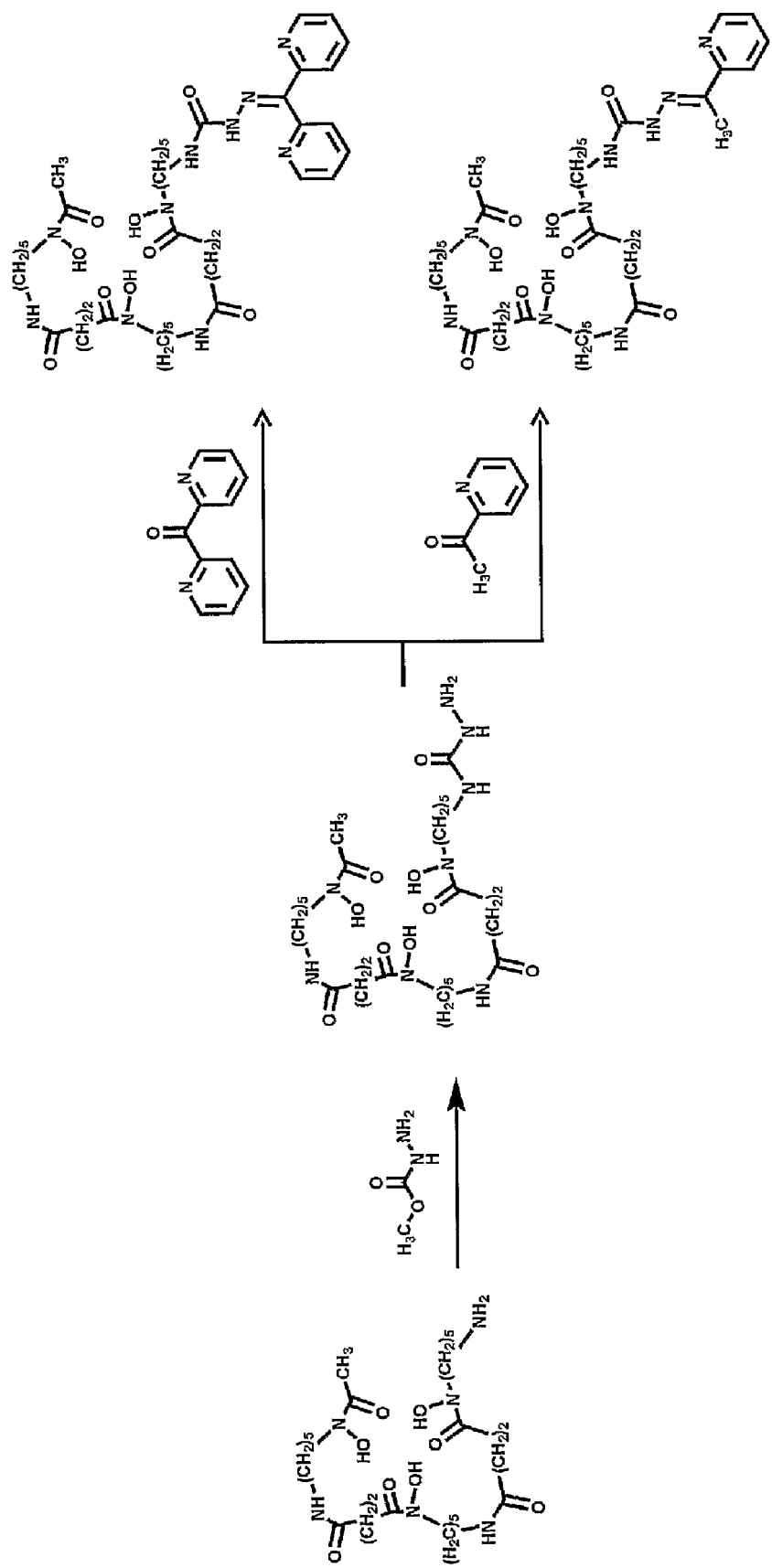
FIG. 20 shows the synthesis of pyridoxal isonicotinyl hydrazone-based derivatives of DFOB.

Analytical RP-HPLC was carried out using a binary pump (Waters) fitted with a Waters Sunfire C18 column (particle size: 5 µm; column dimension: 4.6×150 mm id). The mobile phase comprised of a binary system of: eluent A (100% (v/v) $H_2O$, 0.1% (v/v) TFA) and eluent B (100% (v/v) ACN, 0.1% (v/v) TFA,). A gradient of 100% A to 100% B in 30 min followed by 5 min isocratic elution with B, and finally 10 min isocratic elution with A (total time=45 min), was used at a constant flow rate of 0.2 mL/min. The samples (10 µL) were injected into the column automatically. Samples were prepared at 10 mM concentration (10% (v/v) MeOH, 0.05% (v/v) TFA) and absorbance read at 230 nm (FIG. 20).

Since all of the RP-HPLC experiments were conducted using the same conditions (column, gradient), the retention time of the ligands and of the Fe(III)-loaded ligands provides a relative measure of the hydrophobicity of the compounds (Table 1).

TABLE 1

Retention Times of DFOB, 3-hydroxy-1-acetate-2-methyl-4(1H)-pyridone-DFOB, biotin-DFOB and adamantane-desferrioxamine B in the absence and presence of Fe(III).

|  | DFOB | L1-DFOB | | biotin-DFOB | adamantane-DFOB | |
| --- | --- | --- | --- | --- | --- | --- |
| Retention Time of ligand (min) | 12.04 | I<br>II | 16.99<br>13.15 | 14.53 | III<br>IV | 19.31<br>18.66 |
| Retention time of Fe(III)-loaded ligand (min) | 10.38 | I<br>II | 16.61<br>12.25<br>11.08 | 13.64 | III | 18.65 |

The peaks in the RP-HPLC traces of the free ligands that disappear (shift) in the RP-HPLC traces of the Fe(III)-loaded compounds are attributable to Fe(III)-responsive compounds. Of the four compounds in FIG. 20, DFOB is the most hydrophilic (12.04 min), which correlates with the high water solubility of this compound. The peak attributable to the Fe(III)-loaded DFOB (ferroxamine) shifts to a lower retention time (10.38 min), indicating a greater water solubility of ferroxamine, compared to DFOB. The RP-HPLC trace of Fe(III)-loaded 3-hydroxy-1-acetate-2-methyl-4(1H)-pyridone-DFOB shows three species (16.61, 12.25 and 11.08 min).

TABLE 2

Retention times of standards used in RP-HPLC in FIG. 20.

| Standard | Retention Time (min) | logP |
| --- | --- | --- |
| 4-chloroaniline | 10.37 | 1.8 |
| 3-chlorophenol | 20.425 | 2.4 |
| α-naphthol | 22.22 | 2.7 |
| benzophenone | 25.82 | 3.2 |
| diphenylamine | 28.54 | 3.4 |

The RP-HPLC trace of the free ligand, 3-hydroxy-1-acetate-2-methyl-4(1H)-pyridone-DFOB, shows two major species (16.99 and 13.15 min), which indicates that this complex is not pure and contains a mixture of Fe(III)-chelating compounds, two of which are less water soluble than DFOB. Biotin-DFOB (14.53 min) is less water soluble than DFOB. The peak at 19.31 min in the RP-HPLC trace of adamantane-DFOB is the least water soluble complex from all the complexes studies in this invention thus far. The species giving rise to this peak disappears in the Fe(III)-loaded adamantane-DFOB complex and is, therefore, most likely attributable to adamantane-DFOB. In the RP-HPLC trace of Fe(III)-loaded adamantane-DFOB, the peak at 18.65 min is attributed to Fe(III)-loaded adamantane-DFOB; the retention time of this peak is similar to that for a second peak (18.66 min) which is present in the RP-HPLC trace of adamantane-DFOB. The retention times of a series of standard compounds (as tabled below) were measured under identical conditions to DFOB, 3-hydroxy-1-acetate-2-methyl-4(1H)-pyridone-DFOB, biotin-DFOB and adamantane-desferrioxamine B (Desferadax).

Figure 21:
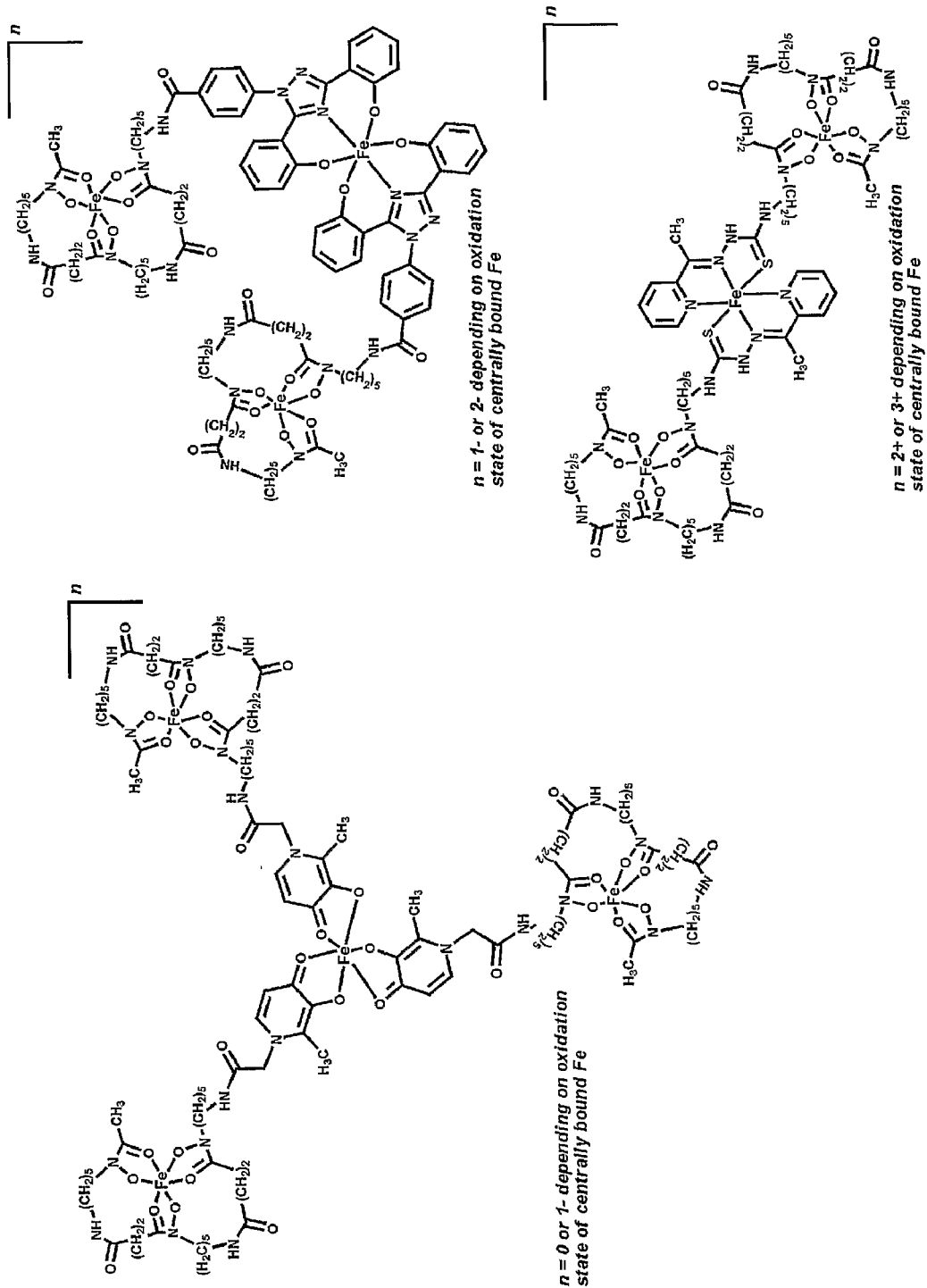
FIG. 21 shows various bifunctional desferrioamine conjugates in accordance with the present invention.

The correlation of this data (FIG. 21) illustrates that adamantane-desferrioxamine B (Desferadax), both and the free compound and Fe(III)-loaded compound is significantly more hydrophobic that DFOB or biotin-DFOB. This may have implications upon the efficiency with which the Fe(III)-loaded complex exits the lipid membrane bilayer.

EXAMPLE 4

Fe(III) Efflux and Fe(III) Uptake Properties of Compounds

The Fe(III) efflux experiments measure the ability of the compound to mobilise $^{59}$Fe from prelabeled SK-N-MC neuroepithelioma cells [13, 14]. The SK-N-MC cells are prelabled for 3 h at 37° C. with $^{59}$Fe-loaded transferrin (0.75 µM) using established techniques [13, 14]. The cell cultures are washed four times with ice-cold phosphate buffered saline and then incubated with the compound (50 µM) for 3 h at 37° C. The radioactive $^{59}$Fe that is released into the overlying media (supernatant) and in the cell pellet is measured using a γ-scintillation counter [15]. The adamantane-DFOB (Desferadax) and 4-methylphenoxyacetate-DFOB compounds are superior Fe efflux agents (28% and 31.6%, respectively), compared to DFOB alone (10.8%) (FIG. 22). Biotin-DFOB and benzo-15-crown-5-4-carboxylate-DFOB are less efficient Fe efflux agents (6.6% and 9.6%, respectively), compared to DFOB. The adamantane-DFOB (Desferadax) and 4-methylphenoxyacetate-DFOB compounds are more efficient at competing with $^{59}$Fe-loaded transferrin for $^{59}$Fe in the extracellular region, thereby preventing accumulation of Fe within the cell (FIG. 23).

EXAMPLE 5

Stability of Compounds

The compounds (biotin-DFOB, adamantane-DFOB, benzo-15-crown-5-4-carboxylate-DFOB or 4-methylphenoxyacetate-DFOB) are likely to be stable over at least the time course of and under the conditions of the Fe efflux and Fe uptake experiments (3 h, 37° C., aqueous). If adamantane-DFOB is susceptible to hydrolysis by amidases, the secondary-amine-based adamantane-DFOB conjugate (see FIG. 24) may be less resistant to the action of amidases, relative to the amide-based adamantane-DFOB compound (Desferadax): this remains untested at this stage. The steric bulk of the adamantane group is very likely to mitigate against the propensity of hydrolysis by amidases in vivo.

EXAMPLE 6

Synthesis of Secondary-Amine-Based Adamantane-DFOB

The PCC-based oxidation of 1-adamantanemethanol will furnish 1-adamantanecarboxaldehyde in an 89% yield, as described in the literature [20]. The Schiff base condensation between 1-adamantanecarboxaldehyde and DFOB will yield the imine-based adamantane-DFOB conjugate which will be reduced by sodium cyanoborohydride (NaCNBH$_3$) to give the secondary amine-based adamantane-DFOB conjugate. Sodium cyanoborohydride does not reduce the hydroxamate groups of DFOB to amides [21].

REFERENCES

[1] Porter, J. B., Rafique, R., Srichairatanakool, S., Davis, B. A., Shah, F. T., Hair, T. and Evans, P. (2005). Recent insights into interactions of deferoxamine with cellular and plasma iron pools: implications for clinical use 1054 (Cooley's Anemia): pp. 155-168.

[2] Ihnat, P. M., Vennerstrom, J. L. and Robinson, D. H. (2000). Synthesis and solution properties of deferoxamine amides 89(12): pp. 1525-1536.

[3] Ihnat, P. M., Vennerstrom, J. L. and Robinson, D. H. (2002). Solution equilibria of deferoxamine amides 91(7): pp. 1733-1741.

[4] Gaasch, J. A., Lockman, P. R., Geldenhuys, W. J., Allen, D. D. and Schyf, C. J. (2007). Brain Iron Toxicity: Differential Responses of Astrocytes, Neurons, and Endothelial Cells 32(7): pp. 1196-1208.

[5] Kalinowski, D. S. and Richardson, D. R. (2005). The evolution of iron chelators for the treatment of iron overload disease and cancer 57: pp. 547-583.

[6] Green, D. A., Antholine, W. E., Wong, S. J., Richardson, D.R. and Chitambar, C. R. (2001). Inhibition of malignant cell growth by 311, a novel iron chelator of the pyridoxal isonicotinoyl hydrazone class: effect on the R2 subunit of ribonucleotide reductase 7(11): pp. 3574-3579.

[7] Chaston, T. B., Lovejoy, D. B., Watts, R. N. and Richardson, D. R. (2003). Examination of the Antiproliferative Activity of Iron Chelators: Multiple Cellular Targets and the Different Mechanism of Action of Triapine Compared with Desferrioxamine and the Potent Pyridoxal Isonicotinoyl Hydrazone Analogue 311 9(1): pp. 402-414.

[8] Rosebrough, S. F. (1993). Plasma stability and pharmacokinetics of radiolabeled deferoxamine-biotin derivatives 265(1): pp. 408-415.

[9] Zhou, M., Haldar, S., Franses, J., Kim, J.-M. and Thompson, D. H. (2005). Synthesis and Self-assembly Properties of Acylated Cyclodextrins and Nitrilotriacetic Acid (NTA)-modified Inclusion Ligands for Interfacial Protein Crystallization 17(1-2): pp. 101-111.

[10] Chan, E. W. S., Chattop adhaya, S., Panicker, R. C., Huang, X. and Yao, S. Q. (2004). Developing Photoactive Affinity Probes for Proteomic Profiling: Hydroxamate-based Probes for Metalloproteases 126: pp. 14435-14446.

[11] Druck, T. P. A. and Burrow, T. E. (2002). Synthesis of feralex a novel aluminum/iron chelating compound 88(1): pp. 19-24.

[12] Devel, L., Rogakos, V., David, A., Makaritis, A., Beau, F., Cuniasse, P., Yiotakis, A., et al. (2006). Development of Selective Inhibitors and Substrate of Matrix Metalloproteinase-12 281(16): pp. 11152-11160.

[13] Richardson, D. R., Tran, E. H. and Ponka, P. (1995). The potential of iron chelators of the pyridoxal isonicotinoyl hydrazone class as effective antiproliferative agents 86(11): pp. 4295-4306.

[14] Baker, E., Richardson, D., Gross, S. and Ponka, P. (1992). Evaluation of the iron chelation potential of hydrazones of pyridoxal, salicylaldehyde and 2-hydroxy-1-naphthylaldehyde using the hepatocyte in culture 15(3): pp. 492-501.

[15] Kalinowski, D. S., Sharpe, P. C., Bernhardt, P. V. and Richardson, D. R. (2008). Structure-Activity Relationships of Novel Iron Chelators for the Treatment of Iron Overload Disease: The Methyl Pyrazinylketone Isonicotinoyl Hydrazone Series 51(2): pp. 331-344.

[16] Bernhardt, P. V., Chin, P., Sharpe, P. C., Wang, J.-Y. C. and Richardson, D. R. (2005). Novel diaroylhydrazine ligands as iron chelators: coordination chemistry and biological activity 10: pp. 761-777.

[17] Whitnall, M., Howard, J. B., Ponka, P. and Richardson, D. R. (2006). A class of iron chelators with a wide spectrum of potent antitumor activity that overcomes resistance to chemotherapeutics 103(40): pp. 14901-14906.

[18] Becker, E. and Richardson, D. R. (1999). Development of novel aroylhydrazone ligands for iron chelation therapy: 2-pyridylcarboxaldehyde isonicotinoyl hydrazone analogs 134(5): pp. 510-521.

[19] Yuan, J., Lovejoy, D. B. and Richardson, D. R. (2004). Novel di-2-pyridyl-derived iron chelators with marked and selective antitumor activity: In vitro and in vivo assessment 104(5): pp. 1450-1458.
[20] Wright, J. A., Gaunt, M. J. and Spencer, J. B. (2006). Novel anti-Markovnikov regioselectivity in the Wacker reaction of styrenes 12(3): pp. 949-955.
[21] Edwards, O. E., Grue-Sørensen, G. and Blackwell, B. A. (1997). Thermolysis and photolysis of two steroidal hydroxamic acids methanesulfonates 75: pp. 857-872.

The claims defining the invention are as follows:

1. A compound of formula (I)

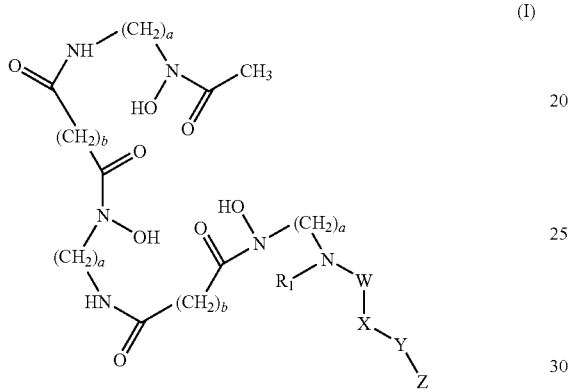

(I)

wherein,
a is an integer from 2 to 7 wherein any of the $CH_2$ groups in this unit can be substituted with alkyl or aryl units that can contain heteroatoms (S, N, O, Cl, F, Br or I);
b is an integer from 1 to 7 wherein any of the $CH_2$ groups in this unit can be substituted with alkyl or aryl units that can contain heteroatoms (S, N, O, Cl, F, Br or I);
$R_1$ is H or $(CH_2)_n$, where n is an integer from 1 to 6 or is a $CH_2$ linker unit that can be further substituted at any $CH_2$ group in the chain with alkyl or aryl units that can contain heteroatoms (S, N, O, Cl, F, Br or I);
W is C(O) or C(S) or $(CH_2)_n$, where n is 0 or an integer from 1 to 6;
X is NH or $(CH_2)_n$, wherein n is 0 or an integer from 1 to 6 or is a $CH_2$ linker unit that can be further substituted at any $CH_2$ group in X with alkyl or aryl units that can contain heteroatoms (S, N, O, Cl, F, Br or I);
Y is absent or is N, O, S, C(O), C(S), S(O), $S(O)_2$, NH or NR' where R' is an alkyl or aryl substituent that can contain heteroatoms (S, N, O, Cl, F, Br or I);
Z is a derivative of 3 hydroxy-1,2-dimethyl-4(1H)-pyridone), a derivative of 4-[3,5-bis(2-hydroxyphenyl)-1H-1,2,4-triazol-1-yl]-benzoic acid) or a carbocycle selected from norbornane, cubane, trishomocubane and adamantane, each of said carbocycle optionally being substituted with at least one substituent, each substituent independently selected from halo, hydroxyl, =O, $C_{1-6}$alkyl, $C_{1-6}$alkyloxy, $C_{1-6}$alkyloxycarbonyl, $C_{1-6}$alkylcarbonyloxy, $C_{1-6}$alkylthio, polyhalo-$C_{1-6}$alkyl, polyhalo$C_{1-6}$alkyloxy, cyano, nitro, carboxyl, $C_{1-4}$alkyl-$SO_2$—, amino, mono- or di($C_{1-4}$alkyl)amino, $C_{1-4}$alkylcarbonylamino, or —$O(CH_2CH_2O)_3$ $CH_2CH_2O$—;

and wherein,
the derivative of 3-hydroxy-1,2-dimethyl-4(1H)-pyridone is

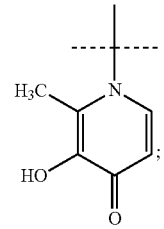

and
the derivative of 4-[3,5-bis(2-hydroxyphenyl)-1H-1,2,4-triazol-1-yl]-benzoic acid is

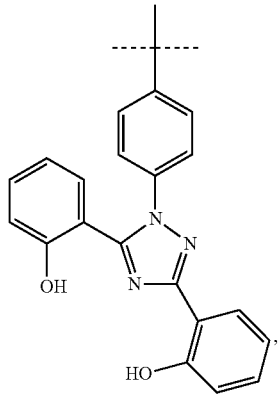

or a pharmaceutically acceptable salt thereof.

2. A compound according to claim 1, selected from:

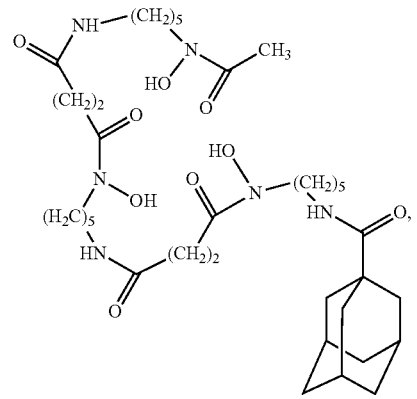

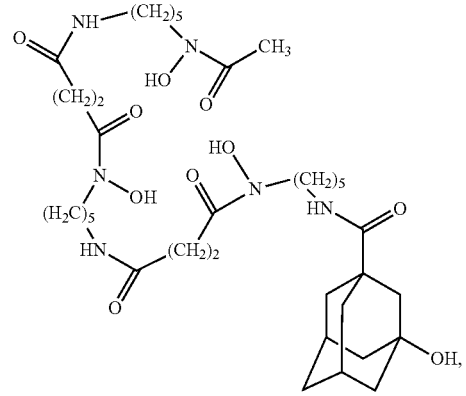

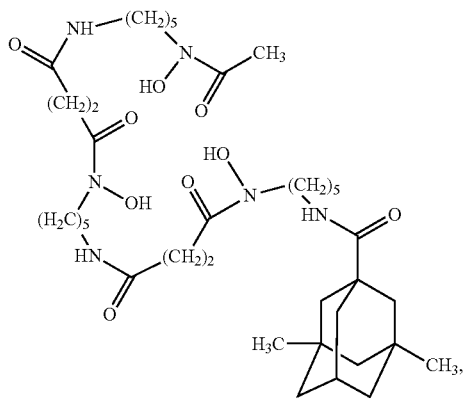
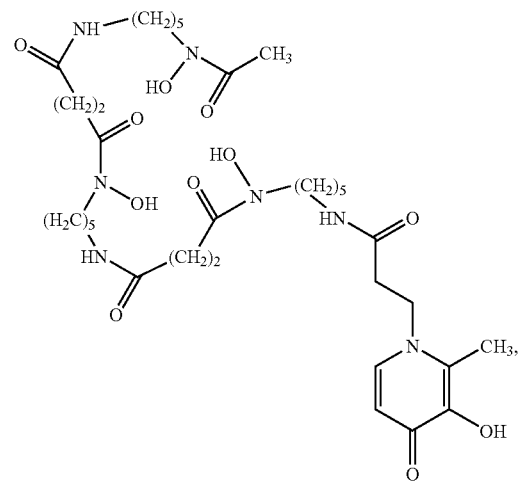
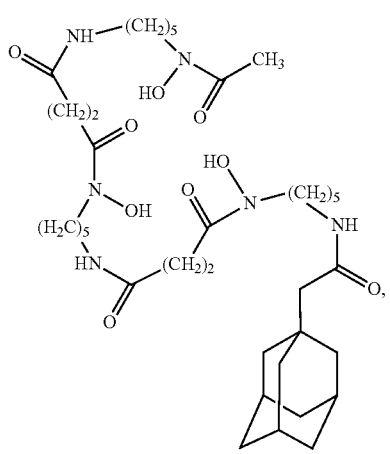
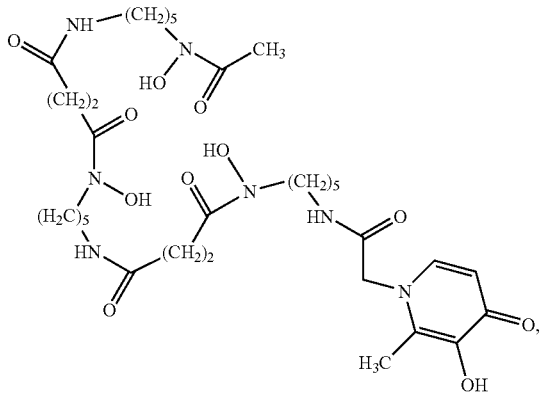
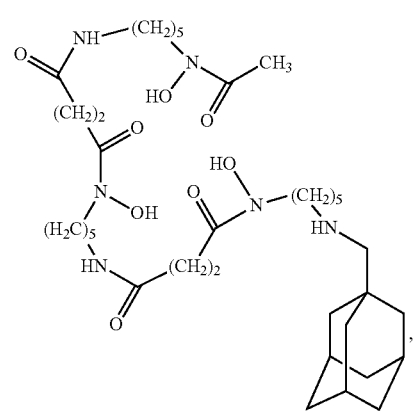
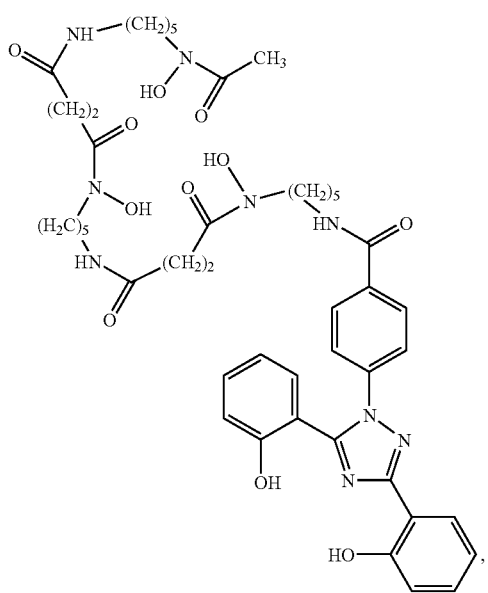
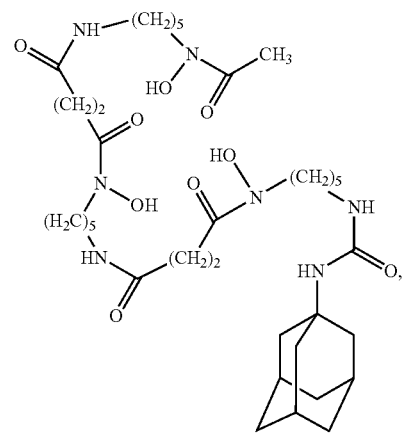

-continued

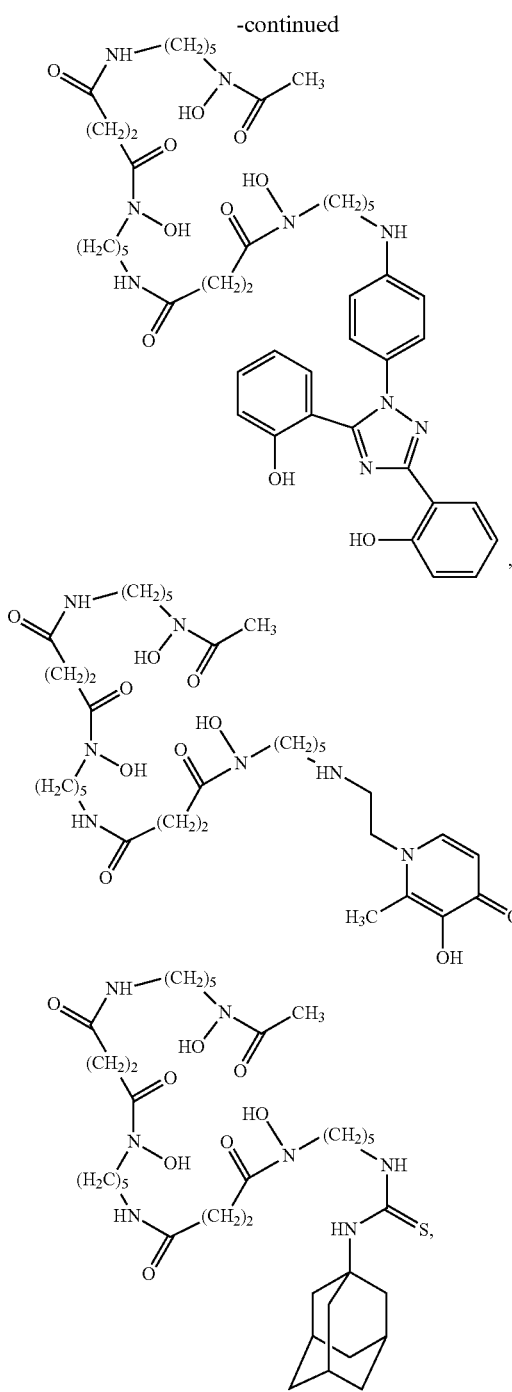

or a pharmaceutically acceptable salt thereof.

3. A method of treating an iron dyshomeostasis disorder comprising administering an effective amount of a compound according to claim 1, or an amide biotin conjugate of formula I, to a patient in need thereof.

4. The method according to claim 3, wherein the iron dyshomeostasis disorder is selected from a primary or secondary iron-overload disorder.

5. The method according to claim 4, wherein the primary iron-overload disorder is selected from Parkinson's disease, Alzheimer's disease, Huntington's disease, haemochromatosis, anaemia, β-thalassaemia, myelodysplastic syndrome, aceruloplasminaemia, Friedreich's ataxia and congenital atransferrinaemia.

6. The method according to claim 5, wherein the haemachromatosis is selected from haemochromatosis type 1, haemochromatosis type 2A, haemochromatosis type 2B, haemochromatosis type 3, haemochromatosis type 4, neonatal haemochromatosis.

7. The method according to claim 5, wherein the anaemia is selected from sickle cell anaemia or Diamond-Blackfan anaemia.

8. The method according to claim 4, wherein the secondary iron-overload disorder is selected from dietary iron overload, long term haemodialysis, chronic liver disease, Hepatitis C infection, alcoholic cirrhosis of the liver, non-alcoholic steatohepatitis or porphyria cutanea tarda.

9. A pharmaceutical composition comprising a compound of formula I:

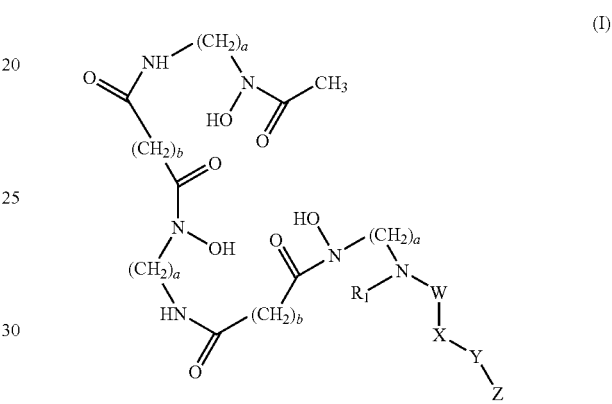

(I)

wherein, a is an integer from 2 to 7 wherein any of the $CH_2$ groups in this unit can be substituted with alkyl or aryl units that can contain heteroatoms (S, N, O, Cl, F, Br or I);

b is an integer from 1 to 7 wherein any of the $CH_2$ groups in this unit can be substituted with alkyl or aryl units that can contain heteroatoms (S, N, O, Cl, F, Br or I);

$R_1$ is H or $(CH_2)_n$, where n is an integer from 1 to 6 or is a $CH_2$ linker unit that can be further substituted at any $CH_2$ group in the chain with alkyl or aryl units that can contain heteroatoms (S, N, O, Cl, F, Br or I);

W is C(O) or C(S) or $(CH_2)_n$, where n is 0 or an integer from 1 to 6;

X is NH or $(CH_2)_n$, wherein n is 0 or an integer from 1 to 6 or is a $CH_2$ linker unit that can be further substituted at any $CH_2$ group in X with alkyl or aryl units that can contain heteroatoms (S, N, O, Cl, F, Br or I);

Y is absent or is N, O, S, C(O), C(S), S(O), $S(O)_2$, NH or NR' where R' is an alkyl or aryl substituent that can contain heteroatoms (S, N, O, Cl, F, Br or I);

Z is a derivative 3 hydroxy-1,2-dimethyl-4(1H)-pyridone), a derivative 4-[3,5-bis(2-hydroxyphenyl)-1H-1,2,4-triazol-1-yl]-benzoic acid) or a carbocycle selected from norbornane, cubane, trishomocubane and adamantane, each of said carbocycle optionally being substituted with at least one substituent, each substituent independently selected from halo, hydroxyl, =O, $C_{1-6}$alkyl, $C_{1-6}$alkyloxy, $C_{1-6}$alkyloxycarbonyl, $C_{1-6}$alkylcarbonyloxy, $C_{1-6}$alkylthio, polyhalo-$C_{1-6}$alkyl, polyhalo$C_{1-6}$alkyloxy, cyano, nitro, carboxyl, $C_{1-4}$alkyl-$SO_2$—, amino, mono- or di($C_{1-4}$alkyl)amino, $C_{1-4}$alkylcarbonylamino, or —$O(CH_2CH_2O)_3CH_2CH_2O$—;

and wherein,
the derivative of 3-hydroxy-1,2-dimethyl-4(1H)-pyridone is
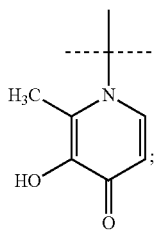
and
the derivative of 4-[3,5-bis(2-hydroxyphenyl)-1H-1,2,4-triazol-1-yl]-benzoic acid is
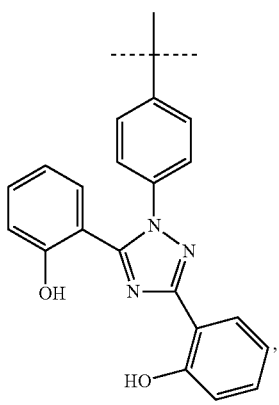
or a pharmaceutically acceptable salt thereof, together with a pharmaceutically acceptable excipient, diluent or carrier.
10. The pharmaceutical composition according to claim 9 selected from:
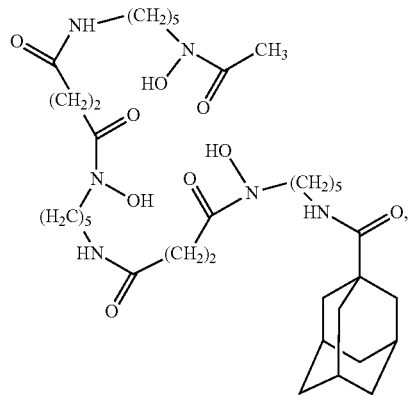
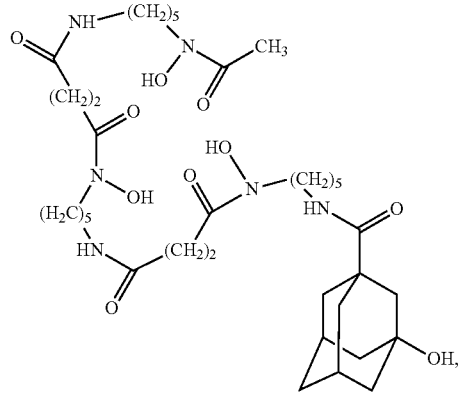
-continued
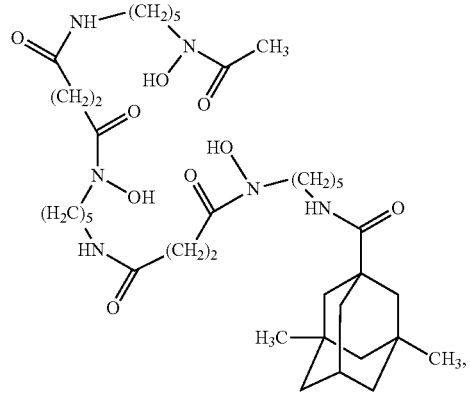
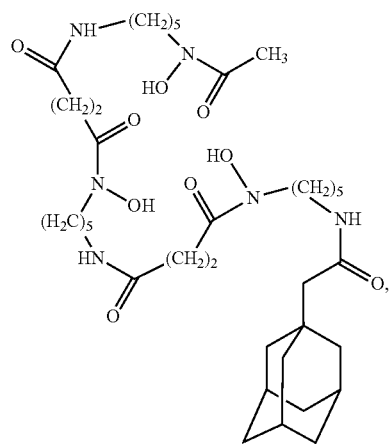
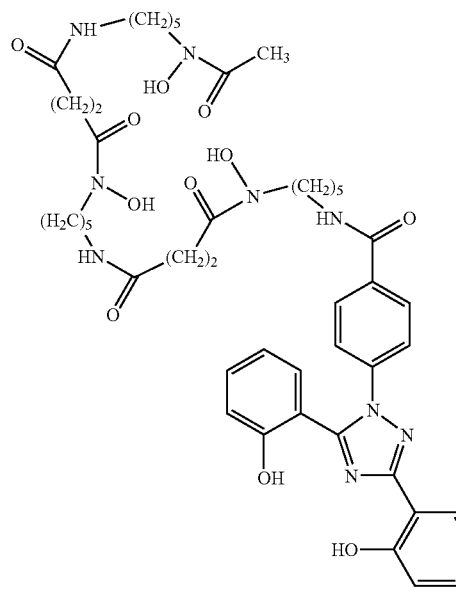

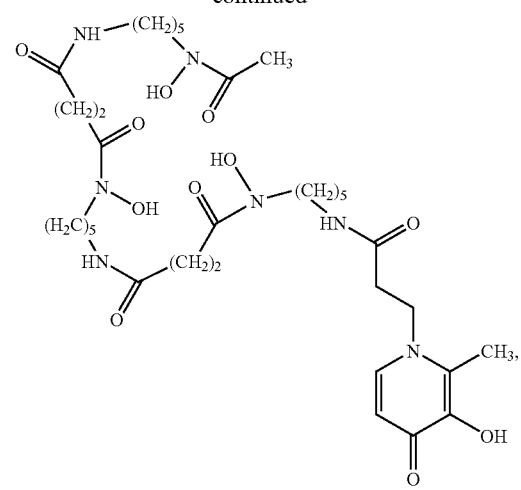
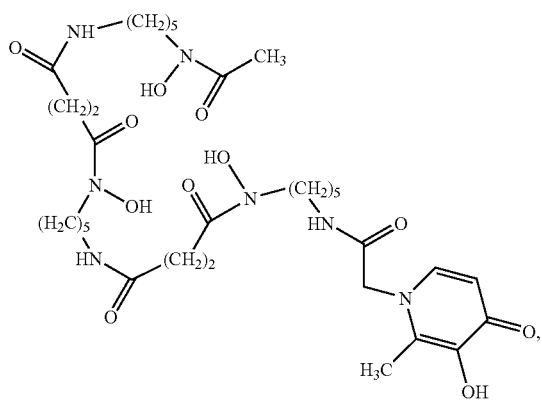
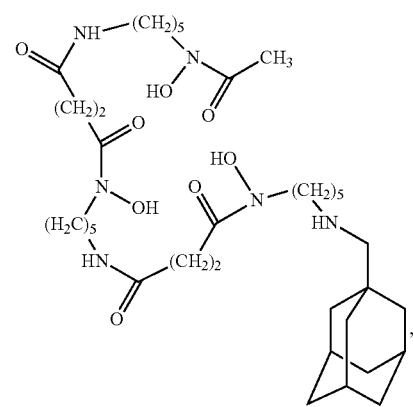
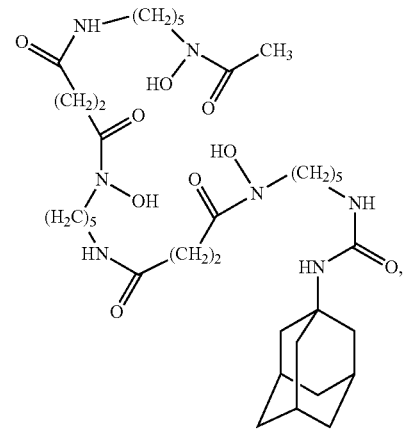

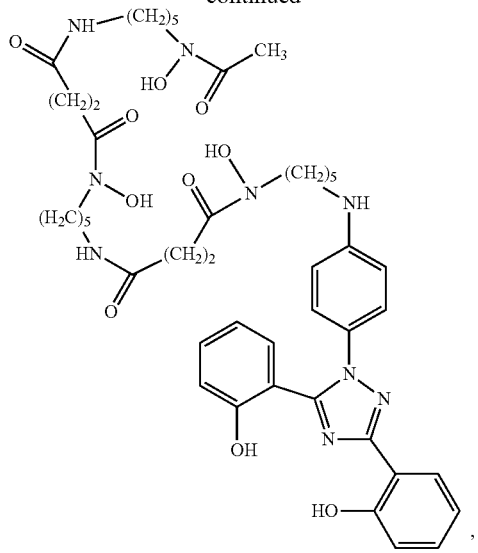
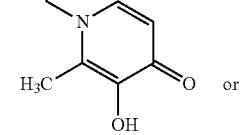
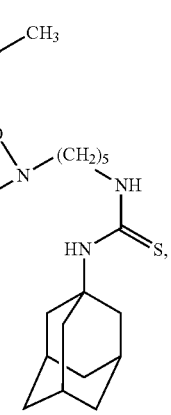

or a pharmaceutically acceptable salt thereof, together with a pharmaceutically acceptable excipient, diluent or carrier.

11. A kit for the treatment of iron overload comprising one or more compounds according to claim 1, or an amide biotin conjugate of formula I, together with instructions for use.

12. A kit for the treatment of a primary or secondary iron-overload disorder comprising one or more compounds according to claim 1, or an amide biotin conjugate of formula I, together with instructions for use.

13. The kit according to claim 12, wherein the primary iron-overload disorder is selected from Parkinson's disease, Alzheimer's disease, Huntington's disease, haemochromatosis, anaemia, β-thalassaemia, myelodysplastic syndrome, aceruloplasminaemia, Friedreich's ataxia and congenital atransferrinaemia.

14. The kit according to claim 13, wherein the haemachromatosis is selected from haemochromatosis type 1, haemochromatosis type 2A, haemochromatosis type 2B, haemochromatosis type 3, haemochromatosis type 4, neonatal haemochromatosis.

15. The kit according to claim 13, wherein the anaemia is selected from sickle cell anaemia or Diamond-Blackfan anaemia.

16. The kit according to claim 12, wherein the secondary iron-overload disorder is selected from dietary iron overload, long term haemodialysis, chronic liver disease, Hepatitis C infection, alcoholic cirrhosis of the liver, non-alcoholic steatohepatitis or porphyria cutanea tarda.

17. A method for reducing iron-overload in a mammal in need thereof, comprising: administering to said mammal an effective amount of one or more compounds according to claim 1, or an amide biotin conjugate of formula I.

* * * * *